(12) United States Patent
Leroux et al.

(10) Patent No.: US 7,938,831 B2
(45) Date of Patent: May 10, 2011

(54) IMPLANT DEVICE

(75) Inventors: Clayton G. Leroux, Avon Lake, OH (US); Robert S. Biscup, Ft. Lauderdale, FL (US)

(73) Assignee: Spineco, Inc., Westlake, OH (US)

( * ) Notice: Subject to any disclaimer, the term of this patent is extended or adjusted under 35 U.S.C. 154(b) by 1609 days.

(21) Appl. No.: 11/210,159

(22) Filed: Aug. 23, 2005

(65) Prior Publication Data

US 2006/0036253 A1 Feb. 16, 2006

Related U.S. Application Data

(63) Continuation-in-part of application No. 10/828,150, filed on Apr. 20, 2004, now Pat. No. 7,615,070.

(60) Provisional application No. 60/609,863, filed on Sep. 14, 2004, provisional application No. 60/650,872, filed on Feb. 8, 2005.

(51) Int. Cl.
*A61F 2/46* (2006.01)
*A61B 17/84* (2006.01)

(52) U.S. Cl. .................. 606/86 R; 606/300

(58) Field of Classification Search .......... 606/301, 606/302, 304, 322, 323, 328, 331, 76–78; 623/18.11, 23.15, 23.16, 23.48, 23.49, 23.5, 623/23.52, 23.55, 23.56, 23.57
See application file for complete search history.

(56) References Cited

U.S. PATENT DOCUMENTS

| | | | |
|---|---|---|---|
| 3,918,440 A | 11/1975 | Kraus | |
| 4,027,392 A | 6/1977 | Sawyer et al. | |
| 4,306,564 A | 12/1981 | Kraus | |
| 4,351,337 A | 9/1982 | Sidman | |
| 4,359,318 A | 11/1982 | Gittleman | |
| 4,378,224 A * | 3/1983 | Nimni et al. | 8/94.11 |
| 4,523,910 A | 6/1985 | Makovich | |
| 4,640,271 A | 2/1987 | Lower | |
| 4,653,489 A | 3/1987 | Tronzo | |
| 4,701,180 A | 10/1987 | Kelly et al. | |
| 4,781,591 A | 11/1988 | Allen | |
| 4,877,019 A | 10/1989 | Vives | |
| 4,886,074 A | 12/1989 | Bisping | |
| 5,116,345 A * | 5/1992 | Jewell et al. | 606/130 |
| 5,129,388 A | 7/1992 | Vignaud et al. | |
| 5,129,900 A | 7/1992 | Asher et al. | |
| 5,292,252 A | 3/1994 | Nickerson et al. | |
| 5,387,212 A | 2/1995 | Yuan et al. | |
| 5,507,814 A | 4/1996 | Gilbert et al. | |
| 5,562,670 A | 10/1996 | Brånemark | |
| 5,571,139 A | 11/1996 | Jenkins, Jr. | |
| 5,584,688 A | 12/1996 | Sakuma et al. | |
| 5,683,391 A | 11/1997 | Boyd | |
| 5,713,904 A * | 2/1998 | Errico et al. | 606/327 |
| 5,725,377 A | 3/1998 | Lemler et al. | |

(Continued)

FOREIGN PATENT DOCUMENTS

DE 4107480 9/1992

(Continued)

*Primary Examiner* — Anu Ramana
(74) *Attorney, Agent, or Firm* — Fay Sharpe LLP; Brian E. Turung

(57) ABSTRACT

An implant and sleeve combination for at least partial insertion into a bone and/or cartilage. The implant includes a lower portion and the sleeve includes a cavity designed to at least partially receive the lower portion of the implant.

30 Claims, 10 Drawing Sheets

U.S. PATENT DOCUMENTS

| | | | |
|---|---|---|---|
| 5,836,935 A | 11/1998 | Ashton et al. |
| 5,871,484 A | 2/1999 | Spievack et al. |
| 5,882,350 A | 3/1999 | Ralph et al. |
| 5,968,098 A | 10/1999 | Winslow |
| 5,989,254 A | 11/1999 | Katz |
| 5,997,539 A | 12/1999 | Errico et al. |
| 6,004,322 A | 12/1999 | Bernstein |
| 6,005,349 A | 12/1999 | Kunhardt et al. |
| 6,017,344 A | 1/2000 | Errico et al. |
| 6,034,295 A | 3/2000 | Rehberg et al. |
| 6,053,917 A | 4/2000 | Sherman et al. |
| 6,056,753 A | 5/2000 | Jackson |
| 6,083,227 A | 7/2000 | Saura et al. |
| 6,113,601 A | 9/2000 | Tatar |
| 6,120,502 A | 9/2000 | Michelson |
| 6,183,472 B1 | 2/2001 | Lutz |
| 6,224,596 B1 | 5/2001 | Jackson |
| 6,319,254 B1 | 11/2001 | Giet et al. |
| 6,340,588 B1 | 1/2002 | Nova et al. |
| 6,368,319 B1 | 4/2002 | Schaefer |
| 6,375,657 B1 | 4/2002 | Doubler et al. |
| 6,402,752 B2 | 6/2002 | Schaffler-Wachter et al. |
| 6,413,260 B1 | 7/2002 | Berrevoets et al. |
| 6,454,807 B1 | 9/2002 | Jackson |
| 6,508,841 B2 | 1/2003 | Martin et al. |
| 6,511,481 B2 | 1/2003 | Von Hoffmann et al. |
| 6,554,830 B1 | 4/2003 | Chappius |
| 6,565,567 B1 | 5/2003 | Haider |
| 6,565,569 B1 | 5/2003 | Assaker et al. |
| 6,565,572 B2 | 5/2003 | Chappius |
| 6,654,629 B2 | 11/2003 | Montegrande |
| 6,669,697 B1 | 12/2003 | Pisharodi |
| 6,778,861 B1 | 8/2004 | Liebrecht et al. |
| 2001/0007074 A1 | 7/2001 | Strobel |
| 2001/0059319 | 7/2001 | Ishida |
| 2001/0053913 A1 | 12/2001 | Freedland |
| 2002/0029043 A1 | 3/2002 | Ahrens et al. |
| 2002/0049394 A1 | 4/2002 | Roy et al. |
| 2002/0095187 A1 | 7/2002 | Thompson et al. |
| 2002/0161367 A1 | 10/2002 | Ferree |
| 2003/0181986 A1* | 9/2003 | Buchholz .................. 623/22.12 |
| 2004/0073221 A1 | 4/2004 | Biscup |
| 2004/0193166 A1 | 9/2004 | Biscup |
| 2004/0243130 A1 | 12/2004 | Biscup |
| 2005/0059972 A1 | 3/2005 | Biscup |
| 2006/0036253 A1 | 2/2006 | Leroux |

FOREIGN PATENT DOCUMENTS

| | | |
|---|---|---|
| EP | 0553 424 A1 | 8/1993 |
| WO | WO 02/076315 A1 | 10/2002 |

* cited by examiner

IMPLANT DEVICE

The present invention claims priority on U.S. Provisional Application Ser. Nos. 60/609,863 filed Sep. 14, 2004 and 60/650,872 filed Feb. 8, 2005, which are incorporated herein by reference. The present invention is a continuation-in-part of U.S. patent application Ser. No. 10/828,150 filed Apr. 20, 2004 now U.S. Pat. No. 7,615,070, which is incorporated herein by reference.

The present invention pertains to prosthetic implants, and more particularly to implants that can be inserted into bone and/or cartilage.

BACKGROUND OF THE INVENTION

The human spine is made up of a column of thirty-three bones and their adjoining structures. The bodies of these vertebrae are connected by anterior and posterior ligaments and by discs of fibrocartilage generally known as intervertebral discs. These discs are positioned between opposite faces of adjacent vertebral bodies. This column of vertebrae and intervertebral discs forms a central axis that supports the head and torso. These vertebrae also enclose an opening through which the spinal cord passes.

One of the most costly health problems in society involves back pain and pathology of the spine. These problems can affect individuals of all ages and can result in great suffering to victims. Back pain can be caused by several factors such as congenital deformities, traumatic injuries, degenerative changes to the spine, and the like. Such changes can cause painful excessive motion, or collapse of a motion segment resulting in the contraction of the spinal canal and compression of the neural structures, causing debilitating pain, paralysis or both, which in turn can result in nerve root compression or spinal stenosis.

Nerve conduction disorders can also be associated with intervertebral discs or the vertebrae themselves. One such condition is herniation of the intervertebral disc, in which a small amount of tissue protrudes from the sides of the disc into the foramen to compress the spinal cord. A second common condition involves the development of small bone spurs, termed osteophytes, along the posterior surface of the vertebral body, again impinging on the spinal cord.

Upon identification of these abnormalities, surgery may be required to correct the problem. For those problems associated with the formation of osteophytes or herniations of the intervertebral disc, one such surgical procedure is intervertebral discectomy. In this procedure, the involved vertebrae are exposed and the intervertebral disc is removed, thus removing the offending tissue or providing access for the removal of the bone osteophytes. A second procedure, termed a spinal fusion, may then be required to fix the vertebrae together to prevent movement and maintain a space originally occupied by the intervertebral disc. Although this procedure may result in some minor loss and flexibility in the spine due to the relatively large number of vertebrae, the minor loss of mobility is typically acceptable.

For the replacement of vertebra of the human spinal column, for the distraction of the spinal column, for the stabilization of the vertebrae and likewise, it is known to apply pedicle screws. The pedicle screw is screwed into the pedicle of the vertebra and the head of the pedicle screw is connected to suitable provisions, for example to a stabilizing system, to distraction rods, etc. During the treatment of the spine, the pedicle screw is generally first rotated into the pedicle. Subsequently, the insertion of the rod is effected.

A standard pedicle screw assembly comprises a screw having an externally threaded stem having in turn a head provided with parts allowing it to be secured to one end of a distraction rod. Typically two such pedicle screws are inserted into respective vertebrae and are secured to a rod to distract and/or stabilize a spinal column after, for instance, a disk operation. One commonly used pedicle screw is disclosed in German Patent No. 4,107,480, which is incorporated herein by reference, and includes a head that has a pair of outwardly projecting parallel ridges with overhanging inner edges. A cap formed with a pair of complementary inwardly open slots fits with these ridges. The pedicle screw is threaded into the vertebrae, an end of the rod is fitted to its outer end, the cap is then slid transverse to the pedicle screw axis and parallel to the rod, over the rod to capture it, and finally a cap screw threaded into the cap and tightened to press the rod down against the head of the pedicle screw and thereby fix the rod, cap, and screw together. Many other pedicle screw designs have been developed to simplify the insertion of the pedicle screw into the pedicle, and/or to reduce damage to the pedicle screw and/or the pedicle during surgery. Some of these pedicle screw designs are disclosed in U.S. Pat. Nos. 5,882,350; 5,989,254; 5,997,539; 6,004,322; 6,004,349; 6,017,344; 6,053,917; 6,056,753; 6,083,227; 6,113,601; 6,183,472; 6,224,596; 6,368,319; 6,375,657; and 6,402,752; and the patents cited and disclosed in such patents. All these designs of pedicle screws are incorporated herein by reference.

After the pedicle screw is inserted in the pedicle, the bone around the pedicle screw must heal to properly secure the pedicle screw in the bone. Any infection that occurs around the pedicle screw can slow the healing process and/or damage the bone around the pedicle screw thereby weakening the connection between the bone and pedicle screw. Typically, a patient is given antibiotics for several days after the surgery to reduce the occurrence of infection about the pedicle screw. The patient may also receive electrical stimulation during surgery to promote the healing process of the bone about the pedicle screw. Both of these techniques have improved the post-operative success of the surgical procedure; however, improved success rates are still needed.

SUMMARY OF THE INVENTION

The present invention pertains to an improved implant, and more particularly to an improved connector (e.g, screw, nail, post, sleeve, etc.). The present invention will be described with particular reference to pedicle screws, nails or posts and a method for use of such pedicle screws, nails or posts; however, it will be appreciated that the invention has much broader applications in that 1) implants other than a screw, a nail or a post can be used in one or more aspects of the invention, and/or b) the implant can be used in many other areas of a body and in many other types of bones.

The implant, when in the form of a screw, nail or post, can be used for insertion into bone and/or cartilage. The screw, nail or post is generally used to anchor and/or affix another type of implant (e.g., rod, cage, stabilization system, etc.) to the bone and/or cartilage; however, the screw, nail or post can be used for other uses such as, but not limited to, attachment of ligaments; connecting and/or repairing fractured and/or broken bones; fusing bones together; reducing pain; stabilizing tissue ligaments, cartilage, and/or bone; retain tissue (e.g., organs, muscle, etc.) in place; an adjunct for another surgical procedure, and the like. As can be appreciated, the implant can have other or additional uses. The implant (e.g., screw, nail, post, etc.) as described herein can be used in repairing a spinal column; however, the implant can be designed to be used in areas of a body other than the spine such as, but are not limited to, acromion, atlas, axis, calcaneus, carpus, clavicle, coccyx, epicondyle, epitrochlea, femur, fibula, frontal bone, greater trochanter, humerus, ilium, ischium, metacarpus, metatarsus, occipital bone, olecranon, parietal bone, patella, phalanx, radius, ribs, sacrum, scapula, sternum, talus, tarsus, temporal bone, tibia, ulna, and/or zygomatic bone.

In one non-limiting aspect of the invention, the implant, when in the form of a screw, nail or post, typically includes a head and a lower portion. The top surface of the head can have a number of different shapes (e.g, flat, sloped, arcuate, circular, polygonal, etc.). The head can have a number of different surfaces (e.g., smooth, rough, ribbed, etc.). The head can have a number of different shapes (e.g., spherical, ellipsoidal, cubic, orthogonal, etc.). The head can have various types of side surfaces (e.g., smooth, rough, ribs, grooves, slots, pits, etc.). The head can include one or more openings; however, this is not required. The head can include one or more connectors; however, this is not required. The head can be rigidly connected to the lower portion, removably connected and/or moveably connected to the lower portion. The shapes, surfaces, connectors, and/or openings of the head, and/or the type of connection between the head and lower portion are generally used to a) facilitate in the insertion and/or removal of the screw, nail or post into bone and/or cartilage, b) facilitate in the attachment and/or disconnection of the head from other components of an implant (e.g., a stabilizing system, distraction rods, cage, mechanical and/or electrical mechanisms, insertion and/or removal tools, etc.), and/or c) facilitate in the operation of the implant and/or components connected to the screw, nail or post. The lower portion of the screw, nail or post can include a threaded outer surface; however, this is not required. The lower portion of the screw, nail or post can have a smooth surface, rough surface, ribs, channels, barbs, teeth, etc. The end of the lower portion of the screw, nail or post can be flat, sharp, forked, etc. The cross-sectional shape and/or area along the length of the lower portion can be constant or can vary. The cross-sectional shape and/or area along the length of the lower portion can be substantially constant or can vary. The cross-sectional shape and/or area along the length of the lower portion can be tapered along at least a portion of the lower portion; however, this is not required. The lower portion can have a number of cross-sectional shapes (e.g., circular, polygonal, oval, arcuate, etc.). The head of the screw, nail or post can be designed to break off after inserting the lower portion into the bone and/or cartilage, and/or an implant; however, this is not required. The lower portion of the screw, nail or post can include a feature (e.g., bore, notch, etc.) which facilitates subsequent removal of the lower portion from the location in which it is secured, and/or facilitate in the connection of more devices to the lower portion; however, this is not required. The lower portion can lie in a single axis or multiple axes. The one or more axes of the lower portion can be fixed; however, this is not required. The one or more axes of the lower portion can be alterable; however, this is not required. In essence, the screw, nail, or post has a configuration that suits the particular application.

In another and/or alternative non-limiting aspect of the present invention, the implant of the present invention can be designed to firmly secure one or more components of an implant to bone and/or cartilage to thereby reduce or prevent rotational or transitional movement of one or more components of the implant. The implant can be designed to be relatively small yet constructed to withstand sufficiently high torque and/or compressive forces to firmly set the implant in the bone and/or cartilage; however, this is not required. The implant can be designed to be easily manipulated to permit relatively rapid insertion and/or tightening during surgical procedures; however, this is not required.

In still another and/or alternative non-limiting aspect of the present invention, the implant can include one or more cavities; however, this is not required. The one or more cavities can be used for a variety of reasons such as, but not limited to, 1) weight distribution of the implant; 2) structural integrity of the implant (e.g., break points, flex points, compression points, etc.); 3) at least partially containing a substance such as, but not limited to, a material that a) promotes and/or inhibits bone and/or other tissue growth, b) inhibits rejection of the implant, c) inhibits rejection of components connected to and/or located adjacent to the implant, d) reduces infection, e) reduces inflammation, f) reduces pain, g) provides vitamins and/or minerals, h) provides genetic material, i) provides tissue, j) promotes healing of surrounding tissue, k) combats or cures cancer and/or other diseases, l) functions as a location and/or visual indicator, and/or the like; and/or 4) at least partially contains one or more electrical and/or mechanical components. When the cavity includes a material, the material in the cavity can be directly contained in the cavity or be at least partially contained within a bladder or bag at least partially positioned in the cavity. An implant that includes one or more cavities that contains a material can be designed to enable the material to at least partially naturally leach out, seep out, flow out, etc. of the implant and/or be designed to at least partially cause the material to exit the implant by use of one or more mechanical and/or electrical devices. When the implant includes two or more cavities, these cavities can be connected together by one or more passageways or remain separate. One or more of the cavities can have at least one access opening to the surface of the implant; however, this is not required. The access opening is generally designed to allow fluids and/or other material to flow into and/or out of the cavity; however, this is not required. The size of the access can be sized to regulate or control the fluid and/or material flow through the access opening (e.g., to control the time release of material from the implant via gravity and/or some other mechanism); however, this is not required. Any number of cavity shapes (e.g., spherical, cylindrical, ovoid, pyramidal, cubical, orthogonal, etc.) and/or sizes can be used. One or more cavities can be located fully or partially in the head and/or lower portion of the implant. One or more substances can be included on and/or in the implant to improve the success of inserting the implant into the bone and/or cartilage, and/or to promote healing about the implant; however, this is not required. These one or more substances, when used, can include, but are not limited to, antithrombogenic agents; steroids; thioprotese inhibitors; antimicrobials; antibiotics; tissue plasma activators; monoclonal antibodies; antifibrosis compounds; hormones; growth factors; anti-mitotic agents; immunosuppressive agents; sense or antisense oligonucleotides; nucleic acid analogues; inhibitors of transcription factor activity; anti-neoplastic compounds; chemotherapeutic compounds; radioactive agents; growth factors; antiplatelet compounds; antitabolite compounds; anti-inflammatory compounds; anticoagulant compounds; antimitotic compounds; antioxidants; antimetabolite compounds; anti-migratory agents; anti-matrix compounds; anti-viral compounds; anti-proliferatives; anti-fungal compounds; anti-rotozoal compounds; human tissue; animal tissue; synthetic tissue; human cells, animal cells; synthetic cells; and/or bone-stimulation, bone-growth and/or bone-activating matter. As can be appreciated, other or additional substances can be used. As can also be appreciated, one or more substances can also or alternatively be included in one or more cavities of the implant; however, this is not required. The one or more substances can be partially or fully coated on the surface of the implant; however, this is not required. The one or more substances can be incorporated in one or more portions of the material that forms the implant; however, this is not required.

In still another and/or alternative non-limiting aspect of the present invention, when one or more access openings are included in the implant, the one or more of the access openings can be used by the manufacturer and/or physician to insert one or more substances into one or more cavities; however, this is not required. As can be appreciated, a physician can add a substance into the cavity just prior to, during, and/or after the insertion of the implant into a patient. As can further be appreciated, a physician can add a substance into the cavity after the surgery has been completed and the patient is recovering from the surgery; however, this is not required. In such a situation, the cavity can be periodically replenished with the same or different substance to facilitate in the recovery of the patient; however, this is not required. The size of one or more of the access openings can be selected to control or regulate the flow of substances into and/or out of the one or more access openings; however, this is not required. One or more cavities can be filled and/or refilled with one or more substances after being inserted in bone and/or cartilage; however, this is not required. The filling and/or refilling of one or more cavities in the implant can facilitate in an ongoing or a sequence of therapies that can be applied at and/or contiguous to the site of insertion of the implant; however, this is not required. One or more access openings can be designed to receive an end of a syringe or other device that is adapted to insert a substance in the access opening; however, this is not required. A tube can be connected between the implant and the surface of the patient's body, which tube includes an opening designed to receive an end of a syringe or other device adapted to insert a substance in the tube opening which in turn conveys the substance to an access opening in the implant; however, this is not required. A cap and/or cover can be applied over one or more access openings; however, this is not required. The cap or cover can be designed to at least partially seal one or more substances in the one or more cavities and/or access openings, and/or to at least partially control the release of one or more substances from the one or more cavities; however, this is not required. The cap or cover, when used, can be made of a biodegradable and/or non-biodegradable material. The cap and/or cover, when used, can be at least partially made of a biodegradable material which at least partially dissolves after the implant has been implanted thereby at least partially providing access to the access opening over time; however, this is not required. The cap and/or cover, when used, can be inserted prior to, during, and/or after the insertion of the implant in the patient. The cap and/or cover, when used, can be designed to be at least partially removed prior to, during, and/or after the insertion of the implant in the patient; however, this is not required. The cap and/or cover, when used, can be at least partially made of a material that allows one or more substances and/or body fluids to penetrate the cap or cover; however, this is not required. The cap and/or cover material can include, but is not limited to, metals, wood, fabric, carbon and/or glass fibers, polymers; copolymers; human tissue; animal tissue; synthetic tissue; human cells; animal cells; synthetic cells; and/or bone-stimulation, bone-growth and/or bone activating matter. As can be appreciated, other or additional materials can be used. The cap and/or cover can be applied to the implant in a number of ways (e.g., dipping, spraying, ionizing, painting, adhesive, screwing, snapping, locking, tacking, soldering, melting, etc.).

In yet another and/or additional non-limiting aspect of the present invention the implant can include one or more outer surface regions that are coated with one or more substances; however, this is not required. The one or more substances include, but are not limited to, a substance that a) promotes and/or inhibits bone and/or other tissue growth, b) inhibits rejection of the implant, c) inhibits rejection of components connected to and/or located adjacent to the implant, d) reduces infection, e) reduces inflammation, f) reduces pain, g) provides vitamins, minerals, and/or nutrients, h) provides genetic material, i) provides tissue, j) facilitates in the insertion, positioning, and/or removal of the implant in the patient (e.g., lubricant, Teflon, graphite, etc.), k) facilitates in securing the implant in a treatment area (e.g., bone, cartilage, bone cement or epoxy or other adhesive, etc.), l) promotes healing of surrounding tissue, m) combats cancer and/or other diseases, n) combats and/or cures biological abnormalities (e.g., chemical imbalance, etc.), o) functions as a location and/or visual indicator, and/or the like. As can be appreciated, the one or more substances can have other or additional uses. The surface of the implant that includes the one or more substances can be smooth, rough (e.g., ribs, canals, pits, teeth, ridges, grooves, holes, notches, slits, slots, channels, corrugations etc.), porous and/or non-porous. The coating, when used, can include a compound that at least partially controls the release of the one or more substances from the coating; however, this is not required. The compound can be biodegradable or non-biodegradable. The coating can be used to facilitate in the insertion and/or securing of the implant; however, this is not required. The coating can include, but is not limited to, polytetrafluoroethylene, or polymers and/or copolymers that includes polytetrafluoroethylene, a natural and/or synthetic bone cement; polymer, co-polymer and/or urethane foam; autologous growth compound; powdered bone, bone and/or other tissue growth stimulating substances; polyglycolate polymers and/or analogues; lactides; polydioxamone; polyglycolate; lactide/glycolide copolymers; and/or other tissue growth inhibiting compounds; and/or other biological agents (e.g., antithrombogenic agents; steroids; thioprotese inhibitors; antimicrobials; antibiotics; tissue plasma activators; monoclonal antibodies; antifibrosis compounds; hormones; growth factors; anti-mitotic agents; immunosuppressive agents; sense or antisense oligonucleotides; nucleic acid analogues; inhibitors of transcription factor activity; anti-neoplastic compounds; chemotherapeutic compounds; radioactive agents; growth factors; antiplatelet compounds; antitabolite compounds; anti-inflammatory compounds; anticoagulant compounds; antimitotic compounds; antioxidants; antimetabolite compounds; anti-migratory agents; anti-matrix compounds; anti-viral compounds; anti-proliferatives; anti-fungal compounds; anti-protozoal compounds; human tissue; animal tissue; synthetic tissue; human cells; animal cells; synthetic cells; and/or bone-stimulation, bone-growth and/or bone activating matter; etc.). The coating material can be applied to the implant by one or more techniques such as, but not limited to, adhesive bonding, welding, soldering, shrink wrapping, melting, spray coating, ionization, hot dipping, electroplating, immersion coating, brush coating, and/or the like. The coating material, when used, can enhance the strength and/or durability of the implant and/or hardens or softens the surface of the implant; however, this is not required. The one or more coatings of one or more substances can be partially or fully coated on the surface of the implant.

In still yet another and/or alternative non-limiting aspect of the present invention, the implant can include at least one opening or mounting member used to connect and/or secure a) one or more devices to anchor and/or affix one or more components of another implant (e.g., rod, cage, stabilization system, screw, post, etc.), and/or b) one or more components of the implant (e.g., connect head to lower portion of implant; connect an electrical and/or electronic component to the implant; connect a mechanical component to the implant; etc.); however, this is not required. The one or more openings can be an access opening as described above, or some other opening; however, this is not required. The one or more mounting members can be, but are not limited to, a ridge, groove, slot, etc. The one or more openings or mounting members, when used, can be positioned on the head and/or lower portion of the screw, nail or post.

In a further and/or alternative non-limiting aspect of the present invention, the implant can include one or more mechanical and/or electrical devices that at least partially cause and/or control the release of one or more substances from the implant; however, this is not required. The mechanical and/or electrical device can be releasably or non-releasably secured to the implant. The mechanical and/or electrical device can be fully or partially embedded in the implant; however, this is not required. The mechanical and/or electrical device can be designed to cause and/or control the release of one or more substances based upon, but not limited to, a) a preprogrammed schedule, b) a function of time, c) a predetermined rate, and/or d) the receipt of an external signal. The mechanical and/or electrical device can be preprogrammed to allow and/or cause the release of one or more substances from the implant during one or more time periods; however, this is not required. The mechanical and/or electrical device can include a microchip that at least partially stores a program that allows and/or causes the release of one or more substances from the implant; however, this is not required. The mechanical and/or electrical device can include one or more MEMS (micro-electro-mechanical systems); however, this is not required. The MEMS, when used, can include both the pre-programming and the mechanism to allow and/or cause the release of one or more substances from the implant; however, this is not required. The microchip, when used, can be designed to at least partially control a separate mechanical and/or electrical device (e.g., valve, pump, motor, etc.) which in turn allows and/or causes the release of one or more substances from the implant; however, this is not required. The microchip can be preprogrammed and/or re-programmed prior to, during and/or after the insertion of the implant; however, this is not required. The parameters for allowing and/or causing the release of one or more substances can be altered by re-programming (e.g., new data, additional data, new source code, additional source code, etc.) during the healing process of a patient, thus are individualized for a patient; however, this is not required. The one or more settings for the mechanical and/or electrical device can be changed, as medical treatment needs dictate (e.g., greater or lesser amounts of substance discharge, different substance discharge ratios, more frequent substance discharge, etc.); however, this is not required. The microchip can be activated prior to, during and/or after the insertion of the implant in a patient; however, this is not required. An external signal can be used to at least partially control and/or alter programming and/or instructions of the microchip and/or other controller of the mechanical and/or electrical device; however, this is not required. The external signal, when used, can include, but is not limited to, an electrical signal, magnetic signal, electromagnetic wave signal (e.g., light, radio wave, microwave, x-ray, infrared light, ultraviolet light, etc.), heat signal, vibration signal, chemical signal, mechanical signal, etc. A transmitter and/or receiver (e.g., wire, fiber optic cable, electromagnetic wave transmitter, etc.) can be connected to the implant and/or be positioned between the implant at or near the surface of the patient's body and/or at some other location to enable the transmitter to transmit a signal from a remote location to the implant. The signal can a) transmit a signal to the mechanical and/or electrical device; b) provide instructions and/or programming to the mechanical and/or electrical device, and/or c) begin or terminate the operation of the mechanical and/or electrical device. As can be appreciated, signals can have other or additional uses. The mechanical and/or electrical device can be activated prior to, during, or after the insertion of the implant in the patient. One or more contact points can be located at or near the surface of the skin of a human or animal, which one or more contacts are connected between a contact surface of the contact point and the implant, and/or one or more components connected to the implant; however, this is not required. The implant, and/or one or more components connected to the implant, can include an electromagnetic wave transmitter and/or receiver which can send and/or receive signals in the form of electromagnetic waves; however, it can be appreciated that the implant can include a transmitter and/or receiver that can transmit and/or receive signals in other or additional forms (e.g., sound waves, etc.). The mechanical and/or electrical device can be activated prior to, during, or after the insertion of the implant in a patent. The mechanical and/or electrical device can at least partially control the location of substance discharge on the implant; and/or control the amount and/or frequency of substance discharge on various regions of the implant; however, this is not required. The mechanical and/or electrical device can open and/or close one or more access openings, and/or cause one or more substances to flow into and/or out of one or more cavities; however, this is not required. When the implant transmits information, the information transmitted from the implant can include, but is not limited to, a) the status of the implant and/or one or more components of the implant; b) the power level of the implant, c) the substance level remaining in the implant, d) operation errors, e) tissue information adjacent to the implant, f) period of time implant has been in patient, g) information about the implant and/or component of the implant, etc. The implant can include one or more memory storage devices to store various types of information; however, this is not required.

In still a further and/or alternative non-limiting aspect of the present invention, the implant can include one or more mechanisms to promote bone healing about the implant and/or adjacent to the implant; however, this is not required. The implant can apply an electrical charge on or about the implant; however, this is not required. Electrical stimulation has been found, in certain situations, to promote the healing of bone and/or other tissue. The use of such electrical stimulation can promote the healing of bone and/or cartilage about the implant. The implant can include one or more mechanical and/or electrical devices that at least partially controls the duration, timing and/or degree of electrical stimulation from the implant; however, this is not required. The mechanical and/or electrical device can be designed to control the duration, timing and/or degree of electrical stimulation based upon a preprogrammed sequence, as a function of time, and/or upon receipt of an external signal; however, this is not required. The mechanical and/or electrical device can be preprogrammed to control the duration, timing and/or degree of electrical stimulation from the implant; however, this is not required. The mechanical and/or electrical device can include a microchip that at least partially stores a program that allows and/or causes the occurrence of an electrical stimulation from the implant; however, this is not required. The mechanical and/or electrical device can include one or more MEMS (micro-electro-mechanical systems); however, this is not required. The MEMS can include both the preprogramming and the mechanism that allows and/or causes the occurrence of an electrical stimulation from the implant; however, this is not required. The microchip, when used, can at least partially control a separate mechanical and/or electrical device (e.g., battery, electric generator, etc.) which in turn allows and/or causes an electrical simulation to occur; however, this is not required. The microchip can be preprogrammed and/or reprogrammed prior to, during and/or after the insertion of the implant. As can be appreciated, the parameters for electrical stimulation can be altered by re-programming (e.g., new data, additional data, new source code, additional source code, etc.) during the healing process of a patient, thus are individualized for a patient; however, this is not required. Consequently, one or more settings for the mechanical and/or electrical device can be changed, as medical treatment needs dictate (e.g., greater or lesser stimulation, a more frequent electrical discharge, adjustments of time and/or power of electrical discharge, etc.). The microchip can be activated prior to, during and/or after the insertion of the implant. The microchip can be activated by an external signal; however, this is not required. The external signal, when used, can include, but is not limited to, an electrical signal, magnetic signal, electromagnetic wave signal (e.g., light, radio wave, microwave, x-ray, infrared light, etc.), heat signal, vibration signal, chemical signal, mechanical signal, etc. The mechanical and/or electrical component can be charged prior to, during and/or after insertion of the implant. The mechanical and/or electrical component can be recharged after insertion of the implant; however, this is not required, such recharging can occur by directly connecting the implant to a power source and/or by a wireless changing arrangement (e.g., use of an electromagnetic wave, etc.); however, this is not required. A transmitter and/or receiver (e.g., wire, fiber optic cable, electromagnetic wave transmitter, etc.) can be connected to the implant and/or be positioned between the implant at or near the surface of the patient's body and/or at some other location to enable the transmitter to transmit a signal from a remote location to the implant. The electric current and/or signal can a) transmit a signal to the mechanical and/or electrical device; b) provide instructions and/or programming to the mechanical and/or electrical device, c) recharge the mechanical and/or electrical device in the screw, nail or post; d) d) generates and/or causes electrical simulation to be generated from the implant, and/or e) begin or terminate the operation of the mechanical and/or electrical device. As can be appreciated, signal can other or additional uses. The mechanical and/or electrical device can be activated prior to, during, or after the insertion of the implant in the patient. One or more contact points can be located at or near the surface of the skin of a human or animal, which one or more contacts are connected between a contact surface of the contact points and the implant, and/or one or more components connected to the implant; however, this is not required. The implant, and/or one or more components connected to the implant, can include an electromagnetic wave transmitter and/or receiver which can send and/or receive signals in the form of electromagnetic waves; however, it can be appreciated that the implant can include a transmitter and/or receiver that can transmit and/or receive signals in other or additional form (e.g., sound waves, etc.). The mechanical and/or electrical device can be activated prior to, during, or after the insertion of the implant in a patent. The electrical stimulation can be at least partially generated by a battery, chemical reaction, generator, magnetic field, electric current, and/or the like. The mechanical and/or electrical device can at least partially control the location of discharge on the implant; and/or control the degree and/or frequency of discharge on various regions of the implant; however, this is not required. The mechanical and/or electrical device can relocate the location of electrical discharge on the implant to promote healing in specified regions about the implant; however, this is not required. The mechanical and/or electrical device can regulate the amount of electrical discharge from one or more regions on the implant to promote healing in specified regions about the implant; however, this is not required.

In still yet a further and/or alternative non-limiting aspect of the present invention, the implant can be designed to be left in place for an indeterminate time after completion of surgery and post-surgical healing and/or can be removed at some time after the completion of surgery, or be replaced during ongoing therapy and/or treatment.

In another and/or alternative non-limiting aspect of the present invention, the implant can be designed to be connected to a mechanical and/or electrical device which mechanical and/or electrical device at least partially regulates and/or controls the discharge of a substance and/or electrical current from at least a portion of the implant; however, this is not required. The mechanical and/or electrical device can be connected to the implant prior to, during, or after insertion of the implant in a patient. The mechanical and/or electrical device can be detachable from the implant prior to, during, or after insertion of the implant in a patient; however, this is not required. The mechanical and/or electrical device can be replaced when it breaks, malfunctions, and/or has completed its useful life, without having to fully or partially remove the implant from a patient; however, this is not required. The implant can include one or more openings, connection locations, and/or contact points for the connection of one or more mechanical and/or electrical devices to the implant; however, this is not required. The one or more openings, connection locations, and/or contact points, when used, can function to secure the mechanical and/or electrical device to the implant, and/or to integrate the mechanical and/or electrical device with one or more cavities and/or other mechanical and/or electrical devices in the implant.

In still another and/or alternative non-limiting aspect of the present invention, the implant, when including a mechanical and/or electrical device, can be designed such that at least a portion of the implant includes the mechanical and/or electrical device; however, this is not required. In one non-limiting design, a majority of the mechanical and/or electrical device can be embedded in the implant prior to, during or after insertion of the implant in a patient. In another non-limiting design, a portion of the mechanical and/or electrical device is embedded in the implant and such portion that is not embedded is designed to be connected to a portion of the mechanical and/or electrical device that is already at least partially formed and/or positioned in the implant.

In yet another and/or alternative non-limiting aspect of the present invention, the implant can be formed of a substantially inert or biologically compatible material for use in humans. The implant can be designed to be used with another implant that is designed to be placed in the intervertebral disc space that was formerly occupied by at least a portion of an intervertebral disc; however, it can be appreciated that the implant can be used with other or additional implants. The implant can be designed to be readily inserted by established surgical procedures, with minimal chances of surgical difficulty; however, this is not required. The implant can be at least partially formed of materials such as, but not limited to, bone, stainless steel, titanium, chromemolybdenum, cobalt chromium alloy, chrome or chrome alloys, cobalt or cobalt alloys, polycarbonate, polypropylene, polyethylene, polymethylmethacrylate, polysolfone types filled with glass and/or carbon fibers, and various types of carbon and fiber reinforced polymers. The material can be wear resistant; however, this is not required. The implant can include one or more openings and/or structures in the head and/or lower portion to facilitate in the positioning of the implant relative to the bone or cartilage and/or to secure the implant in the patient. One or more of the openings and/or structures in the implant can be adapted to receive an instrument for guiding, inserting, and/or removing the implant in the patient. Further details of the implant are set forth in United States Patent Publication No. 2004/0243130, which is incorporated herein.

In a further and/or alternative non-limiting aspect of the present invention, the implant can be designed to be at least partially connected to the bone and/or cartilage after an opening in the bone and/or cartilage has been formed; however, this is not required. When an opening or hole is formed, such opening or hole can be formed by a drill or similar device; however, this is not required. The size of the opening or hole can be selected to be larger, smaller or the same size as the cross-sectional area of the implant. The opening or hole can be inserted in the bone and/or cartilage to reduce damage to the bone and/or cartilage when the implant is subsequently inserted in the bone and/or cartilage, and/or to provide a guide opening for insertion of the implant; however, this is not required.

In a still further and/or alternative non-limiting aspect of the present invention, a sleeve can be used in conjunction with one or more implants. When an opening or hole is formed in the bone and/or cartilage, the sleeve can be designed to be at least partially inserted into the opening or hole prior to or during the insertion of the implant in the bone and/or cartilage; however, this is not required. As can be appreciated, the sleeve can designed to be partially or fully inserted into the bone and/or cartilage with a hole or opening being first inserted into the bone and/or cartilage. The sleeve can be designed to be a temporary or permanent device. When the sleeve is a temporary device, the sleeve can be designed to be at least partially inserted in the bone and/or cartilage and then removed prior to the insertion of the implant into the bone and/or cartilage; however, this is not required. When the sleeve is inserted into a preformed hole or opening in the bone and/or cartilage, and/or the sleeve is used to at least partially form a hole or opening in the bone and/or cartilage, the sleeve can be used to a) inhibit or prevent contamination of the formed opening or hole in the bone and/or cartilage, b) inhibit or prevent growth of tissue and/or bone in the formed opening or hole, c) allow time for the bone and/or tissue around the opening or hole to at least partially heal (e.g., 1-20 weeks), d) facilitate in connecting or securing the implant to the bone and/or cartilage, e) enable one or more implants that are at least partially connected to the sleeve to be unsecured and/or disconnected from the sleeve with minimal, if any, damage to the surrounding bone and/or cartilage (i.e., minimally-invasive), and/or f) enable one or more implants that are at least partially secured to the sleeve to be replaced with one or more other implants with minimal, if any, damage to the surrounding bone and/or cartilage (i.e., minimally-invasive). As can be appreciated, there can be other uses for this temporary or removable sleeve. The sleeve can also be a permanent or non-removable device that is designed to be maintained in the opening or hole formed in the bone and/or cartilage. In such a use, the sleeve can be used to a) inhibit or prevent contamination of the formed opening or hole in the bone and/or cartilage, b) inhibit or prevent growth of tissue and/or bone in the formed opening or hole, c) allow time for the bone and/or tissue around the opening or hole to at least partially heal (e.g., 1-20 weeks), d) facilitate in connecting or securing the implant to the bone and/or cartilage, e) enable one or more implants that are at least partially connected to the sleeve to be unsecured and/or disconnected from the sleeve with minimal, if any, damage to the surrounding bone and/or cartilage (i.e., minimally-invasive), and/or f) enable one or more implants that are at least partially secured to the sleeve to be replaced with one or more other implants with minimal, if any, damage to the surrounding bone and/or cartilage (i.e., minimally-invasive). As can be appreciated, other uses can be used for this permanent or non-removable sleeve. The sleeve can be inserted by a variety of techniques such as, but not limited to, percutaneous insertion, computerized image guidance, stereo-static imaging, robotic surgery, etc.

In yet a further and/or alternative non-limiting aspect of the present invention, the sleeve can include one or more cavities designed to receive at least a portion of one or more implants prior to, during and/or after the sleeve is at least partially inserted into the bone and/or cartilage. The one or more of the cavities can include one or more structures (e.g., threads, ribs, grooves, notches, spikes, barbs, protrusions, openings, slots, indentations, etc.) that are used to facilitate in the connection and/or removal of one or more implants to/from the one or more cavities; however, this is not required. The one or more cavities of the sleeve can also or alternatively be used to a) contain one or more substances (e.g., medicine and/or other biological agents, etc.), b) facilitate in connecting the implant in the cavity, and/or c) facilitate in the insertion and/or securing and/or removal of the sleeve into/from the bone and/or cartilage. As can be appreciated, the cavity of the sleeve can be used for other and/or additional reasons. The cavity of the sleeve can have a generally uniform cross-sectional shape along the longitudinal length of the cavity or the cross-sectional shape can vary along the longitudinal length of the cavity. The cross-sectional shape of the cavity can have a variety of shapes (e.g., circular, polygonal, oval, arcuate, etc.).

In still yet a further and/or alternative non-limiting aspect of the present invention, the sleeve can include can include one or more openings to facilitate in the flow of materials out of and/or into the sleeve, facilitate in exposing the surrounding tissue and/or bone to a current, etc; however, this is not required. For instance, one or more substances (e.g., medicine and/or other biological agents, etc.) can be inserted into one or more openings and/or cavities and/or passageways in the sleeve prior to, during and/or after the at least partial insertion of the sleeve in the opening or hole in the bone and/or cartilage. The one or more substances that are inserted into one or more openings and/or cavities and/or passageways in the sleeve can be the same or similar substances that can be used with and/or coated on the implant as previously described above (e.g., powdered bone, cartilage, cement or epoxy and/or other type of adhesive, medicine and/or biological agent, etc.); however, this is not required. In such an arrangement, the sleeve can function as a partial conduit for the transmission of one or more substances to and/or about the bone and/or cartilage that is in contact with and/or positioned in close proximity to the location of the sleeve. The size and/or shape of the one or more openings and/or cavities and/or passageways in the sleeve can be used to at least partially control the rate at which one or more substances are released from the sleeve; however, this is not required. As can be appreciated, the one or more openings can be used for other and/or additional reasons. When one or more substances that are inserted into one or more openings and/or cavities and/or passageways in the sleeve, the insertion of one or more substances can be accomplished by a variety of means. In one non-limiting means, one or more substances are pumped into one or more openings and/or cavities and/or passageways in the sleeve prior to, during and/or after the at least partial insertion of the sleeve in the opening or hole in the bone and/or cartilage. In another non-limiting means, the sleeve includes one or more bladders and/or balloons that are at least partially filled with one or more substances prior to, during and/or after the at least partial insertion of the sleeve in the opening or hole in the bone and/or cartilage. As can be appreciated, many other or additional means can be used. As can also be appreciated, one or more substances can be at least partially inserted into one or more openings and/or cavities and/or passageways in the sleeve prior to/during and/or after the at least partial connection of an implant to the sleeve; however, this is not required. In another and/or alternative non-limiting example, the one or more openings and/or cavities and/or passageways in the sleeve can include one or more current generating mechanism to continuously and/or periodically and/or controllably generate a current to facilitate in the promotion of healing about the sleeve. One or more portion of the sleeve can include and/or be formed of a current conducting material to at least partially facilitate in the transmission of current to and/or about certain portions of the sleeve; however, this is not required.

In another and/or alternative non-limiting aspect of the present invention, the sleeve can include and/or be at least partially coated with at least one substance (medicine and/or biological agent, etc.), and/or be designed to receive at least one substance; however, this is not required. The one or more substances, when used, can be used for a variety of reasons such as, but not limited to, improving the success of retaining the sleeve and/or implant in the bone and/or cartilage; reducing the rejection of the implant, another implant and/or sleeve; reducing or inhibiting infection from the insertion of the implant, another implant and/or sleeve; reducing inflammation; reducing pain; providing vitamins, minerals, and/or nutrients; providing genetic material; providing tissue; facilitating in the insertion, positioning, and/or removal of the implant in the patient; promoting healing of surrounding tissue; combating cancer and/or other diseases; combating and/or cures biological abnormalities; functioning as a location and/or visual indicator, and/or the like. As can be appreciated, the one or more substances can be used for other and/or additional reasons.

In still another and/or alternative non-limiting aspect of the present invention, the sleeve can be at least partially formed of a biodegradable material, a bioabsorbable material, a non-biodegradable material, and/or a non-bioabsorbable material. In one non-limiting design, the sleeve is at least partially formed of materials such as, but not limited to, bone, stainless steel, titanium, chromemolybdenum, cobalt chromium alloy, chrome or chrome alloys, cobalt or cobalt alloys, polycarbonate, polypropylene, polyethylene, polymethylmethacrylate, polysolfone types filled with glass and/or carbon fibers, and various types of carbon and fiber reinforced polymers.

In yet another and/or alternative non-limiting aspect of the present invention, the sleeve can include a removable cap; however, this is not required. The cap, when used, can be used to at least partially cover or seal an internal cavity of the sleeve; however, this is not required. The cap, when used can be formed of a material, or includes one or more openings to enable the flow of one or more materials into and/or out of the sleeve; however, this is not required, when the cap includes one or more openings, the one or more openings can have a size and/or configuration to at least partially control the flow rate of one or more substances through the cap; however, this is not required. The cap can be used in conjunction with the sleeve to at least partially cover the cavity of the sleeve and/or facilitate in the insertion and/or securing and/or removal of the sleeve into/from the bone and/or cartilage; however, this is not required. The cap can include one or more slots, openings, ribs, threads, etc., to facilitate in the connection to and/or removal from the sleeve. The outer surface of the sleeve can be smooth; however, this is not required. The outer surface of the sleeve can include one or more non-smooth surfaces (e.g., spikes, barbs, "bayonet" joinder, threads, cavities, protrusions, openings, slots, ribs, indentations, grooves, etc.) to facilitate in the connection of the sleeve to the bone and/or cartilage; however, this is not required.

In still yet another and/or alternative non-limiting aspect of the present invention, the sleeve can include one or more components (e.g., slots, ribs, indentations, grooves, threads, notches, spikes, barbs, protrusions, openings, indentations, etc.) used to facilitate in the insertion and/or securing and/or removal of the sleeve to/from the opening or hole in the bone and/or cartilage; however, this is not required. In one non-limiting design, the sleeve can include one or more side slots to form a split type sleeve; however, this is not required. In such a design of the sleeve, a component such as a cap, an implant, a set screw, etc. can be inserted in an opening or hole or cavity of the sleeve to cause the one or more slots to enlarge thereby resulting in the sleeve to be better secured in the opening and/or hole in the bone and/or cartilage. This design could also be used to reduce the size of the one or more slots in the sleeve to facilitate in the removal of the sleeve from the bone and/or cartilage; however, this is not required.

In a further and/or alternative non-limiting aspect of the present invention, the sleeve can have a uniform or non-uniform size and/or shape. The cross-sectional shape of the sleeve can be generally circular; however, other shapes can be used (e.g., circular, oval, polygonal, curvilinear, etc.). The three dimensional shape of the sleeve can have a variety of shapes (e.g., cylindrical, spherical, pyramid, cube, prism, egg-shaped, parallelepiped, conical, etc.). The sleeve can have a uniform or varied cross-sectional area along the longitudinal axis of the sleeve.

In still a further and/or alternative non-limiting aspect of the present invention, the sleeve can include one or more markers (visual marker, radiopaque marker, etc) to facilitate in a) the positioning of the sleeve in the bone and/or cartilage, and/or b) to monitor the position of the sleeve in the bone and/or cartilage. The one or more markers can also be used to ensure that the sleeve has been properly inserted a proper depth into the opening in the bone and/or cartilage. As can be appreciated, the one or more markers can have other or additional functions. The markers can be located on the outside surface of the sleeve, the inside surface of the sleeve, imbedded in the sleeve, etc. As can be appreciated, the implant can also or alternatively include one or more markers to facilitate in a) the positioning of the implant in the sleeve, and/or b) to monitor the position of the implant in the sleeve. As can be appreciated, the cap for use with the sleeve can also or alternatively include one or more markers to facilitate in a) the positioning of the cap in the sleeve, and/or b) to monitor the position of the cap in the sleeve.

In yet a further and/or alternative non-limiting aspect of the present invention, the sleeve can be formed of at least two components, namely an outer sleeve and an inner attachment. The outer sleeve can include one or more of the following non-limiting features:
  Can have various sizes and/or shapes to conform to the vertebral pedicle anatomy.

Can have a generally hollow center or cavity.

Can have a fixed or expandable distal tip for enhanced fixation.

Can includes a porous coated material.

Can be formed of a variety of materials (e.g., metal, ceramic, memory metals, polymer, etc.).

Can be coated with hydroxy appetite, BMP, and/or other bone forming stimulant.

Can include a removable temporary cap or filler-post to inhibit or prevent bone in-growth in the hollow center or cavity of the sleeve. The removable temporary cap or filler-post can be re-inserted if necessary so that the sleeve can be re-visited in the future.

Can be used to at least partially anchor and/or be attach to a variety devices or attachments once bone ingrowth has at least partially occurred.

The Outer Sleeve can be designed to substantially permanently stay in the bone and/or cartilage.

The inner attachments to the outer sleeve can be and/or include one or more of the following non-limiting features:

Can have a modular head (e.g., straight threaded post, polyaxial head, open "tulip head", etc.)

Can be vertebral body implants/devices.

Can include or be a micro medicine delivery system (e.g., chemotherapy, antibiotics, bone growth, hormone stimulators, stem cells, pain managements medications, etc).

Can be or include an electrical stimulation device.

Can include an expandable device (e.g., balloons, memory metals, polymers, etc.).

Can include a mechanical sensor.

Can be or include motion preservation devices (e.g., artificial facets, stabilization bands, expandable growth rods, flexible devices, etc.).

Can be designed to be secured to the outer sleeve by a variety of mechanisms (e.g, machine thread, press-fit, captured ball-bearings, twist-lock, etc.).

Can be designed to be removable or permanently attachable to the outer sleeve (e.g., filler post re-inserted, etc.).

Various non-limiting applications of the sleeve include:

A bone anchor for motion preservation surgery with artificial facets, stabilization bands, flexible rods and/or plates. Standard pedicle screws commonly loosen and/or deform over time. The use of the sleeve overcomes this problem.

Degenerative spine disease.

Spinal fractures.

Tumors.

Scoliosis and other deformity surgery.

Failed fusion and revision spine surgery.

One non-limiting technique that can be used in association with the sleeve includes:

1. Preoperative planning including number of pedicles, levels, and vertebrae to be treated.
2. Outer sleeve inserted under general, spinal, or local anesthesia. The outer sleeve could be inserted by a variety of one or more techniques including, but not limited to, percutaneous insertion, computerized image guidance, stereo-tactic imaging, robotic surgery, etc.
3. Fixed or expandable distal tip for outer sleeve used.
4. Image guidance is used for proper location and insertion site for outer sleeve.
5. Temporary filler post or cap inserted into opening or cavity of outer sleeve prior to completion of surgery. The temporary filler post or cap could be inserted by a variety of one or more techniques including, but not limited to, percutaneous insertion, computerized image guidance, stereo-tactic imaging, robotic surgery, etc.
6. Patient is discharged.
7. Bio-ingrowth of outer sleeve occurs and determined by imaging studies and/or other techniques. Such bio-ingrowth occurs within about 4-8 weeks.
8. Second and definitive surgery performed by removing temporary filler post or cap from outer sleeve and then re-inserting preselected inner attachment(s). Additional devices (e.g., rods, plates, motion preservation devices, etc) can then be attached to inner attachment, if desired, depending on the goals of surgery. The temporary filler post or cap could be removed/inserted by a variety of one or more techniques including, but not limited to, percutaneous insertion, computerized image guidance, stereo-tactic imaging, robotic surgery, etc.

Specialized instruments and insertion tools (e.g., robotics, hand tools, etc.) can be developed specifically for the insertion of the outer sleeve, insertion/removal of temporary filler, insertion/removal of inner attachment(s) during surgery. Computerized software for pre-operative planning and intraoperative use can be developed.

In still yet a further and/or alternative non-limiting aspect of the present invention, the sleeve, when used, can be designed to be inserted at one period of time, and the surgery involving the implant can be done at another period of time. The sleeve can be inserted by a variety of techniques such as, but not limited to, percutaneous insertion, computerized image guidance, stereo-static imaging, robotic surgery, etc. For instance, one or more sleeves can be inserted into one or more bones or cartilage having openings formed thereon. In this non-limiting procedure, the one or more sleeves could be inserted by day surgery or outpatient surgery; however, longer visits could be required. This procedure could be completed by a technician or surgeon other than the surgeon that is perform the "main" surgery involving the implant; however, this is not required. After the one or more sleeves are inserted, the bone and tissue about the sleeve could be allowed to heal over the course of several days or weeks. If the one or more sleeves are semi-permanent or permanent sleeves, one to several weeks (e.g., 1-8 weeks) or months (e.g., 1-8 months) may be allowed to pass after the one or more sleeves are inserted before further procedures involving the sleeves are conducted. Once a sufficient period of time has passed, an implant can be inserted into the one or more sleeves or the sleeves can be removed prior to the implant being inserted into the bone and/or cartilage. The procedure for inserting one or more implants and/or removing one or more sleeve could also be done by day surgery or outpatient surgery; however, longer visits could be required. As can be appreciated, the prior insertion of the sleeve has one non-limiting advantage of being able to be at least partially inserted into the bone and/or cartilage prior to the "main" surgery. As such, the person inserting the sleeve at least partially inserted into the bone and/or cartilage can be a lesser skilled surgeon or technician than the surgeon that is to perform the "main" surgical procedure that involves the devices used with and/or in conjunction with the sleeve. Consequently, this procedure can be less expensive for a patient and/or enable a surgeon to focus his/her skills on more complicated and/or technically intensive procedures. Another and/or alternative non-limiting advantage for using a sleeve is that the use of the sleeve can result in a smaller hole and/or opening in to be utilized during the "main" surgical procedure. A opening and/or hole in the bone and/or cartilage is commonly formed prior to the insertion of the sleeve into such opening or hole. The sleeve can be inserted by a variety of techniques such as, but not limited to, percutaneous insertion, computerized image guidance, stereo-static imaging, robotic surgery, etc. After the sleeve has been at least partially inserted into the opening or hole and after the bone and/or cartilage has grown about the sleeve so as to "set" the sleeve in the bone and/or cartilage, the smaller opening in the sleeve allows for a more precise and/or secure and/or stronger connection of one or more components to the sleeve than if such components were merely connected directly to the bone and/or cartilage. The smaller opening in the sleeve can be closed by used of a cap, post, etc. to inhibit or prevent fluids and/or tissue growth in the cavity of the sleeve; however, this is not required. When a cap, post, etc is used, such cap, post, etc can be removed after the bio-ingrowth has occurred with respect to the sleeve. The cap, post, etc can be removed by a variety of techniques such as, but not limited to, percutaneous insertion, computerized image guidance, stereo-static imaging, robotic surgery, etc. The smaller opening of the sleeve as compared to the opening or hole in the bone and/or cartilage that was used to at least partially receive the sleeve results in a more "minimally-invasive" procedure during the "main" surgery. As such, the use of the sleeve has the significant advantage of allow for a more "minimally-invasive" procedure during the "main" surgery than surgical procedures that do not utilize the sleeve. Consequently, the use of the sleeve can a) improve recovery rates of a patient after the surgical procedure, b) improve the success of the surgical procedure, and/or c) reduce the invasiveness of the surgical procedure. As can be appreciated, the use of the sleeve can have other and/or additional advantages. It is possible to use the sleeve to conveniently remove a support system from the vertebra or other regions in the body once the desired amount of healing has occurred, and/or to insert one or more differently configured implants during a progressive procedure (e.g., the gradual straightening of the spine, etc.). When the implant is to be removed from the patient, the implant could be removed from the body and one or more sleeves could be left in the patient; however, this is not required. If the sleeves are bioabsorbable or biodegradable, the sleeves can be designed to dissolve and/or be bodily absorbed. The sleeve could also, or alternatively, be designed such that the implant is partially or fully inserted into the sleeve prior to the sleeve being partially or fully inserted into the bone and/or cartilage. In one situation using this arrangement, the implant can simply be inserted with the sleeve into the bone and/or cartilage, thus eliminating a two step process of first inserting the sleeve and then after, inserting the implant into the sleeve; however, this is not required. In one non-limiting configuration, the sleeve could include notches or "teeth" or other non-smooth surfaces that can be used to engage or lock with one or more non-smooth surfaces on the implant; however, this is not required. As can be appreciated, the sleeve can have many other or additional configurations. It is also and/or alternatively possible to use the one or more sleeves to allow the replacement and/or reconfiguration of one or more implants. For instance, when one or more implants are used to at least partially supply and/or inject one or more substances into and/or about a particular body region and/or being used to provide electro-stimulation into and/or about a particular body region, the pump in such implant may fail and/or need to be replaced, one or more substances (e.g., medicine and/or biological agent, etc.) may need to be replenished and/or changed, the battery may fail and/or need to be replaced, and/or the implant may be damage and need to be replaced, the use of a sleeve facilitates in the removal and insertion of the implant into and out of the sleeve. In addition or alternatively, when one or more implants have carried out the set task and need to be reconfigured and/or replace with one or more other implants to accomplish a new task, the use of a sleeve facilitates in the removal and insertion of the implant into and out of the sleeve. The removal/insertion procedure could be done by day surgery or outpatient surgery; however, longer visits could be required.

It is one non-limiting object of the present invention to provide an improved implant and sleeve combination for use in bone and/or cartilage.

It is another and/or alternative non-limiting object of the present invention to provide an implant and sleeve combination that can be easily and efficiently positioned into bone and/or cartilage and which reduces the failure rate of prosthetic implants.

It is still another and/or alternative non-limiting object of the present invention to provide an implant and sleeve combination designed to simplify the insertion and affixing of an implant in the bone and/or cartilage.

It is yet another and/or alternative non-limiting object of the present invention to provide a sleeve that can be at least partially inserted into an opening in bone and/or tissue and can be used to facilitate in the removal and/or insertion of an implant from a sleeve.

It is still yet another and/or alternative non-limiting object of the present invention to provide a sleeve that can be at least partially inserted into an opening in bone and/or tissue and allowed to at least partially adhere to the bone and/or tissue over a period of time prior to insertion of the screw, nail, or post from/into the sleeve.

It is a further and/or alternative non-limiting object of the present invention to provide a sleeve that can be used to facilitate in the removal of an implant from the sleeve and/or insertion of a replacement implant from/into the sleeve.

It is still a further and/or alternative non-limiting object of the present invention to provide a sleeve that includes one or more markers.

These and other objects of the invention will become apparent to those skilled in the art upon reading and understanding the following detailed description of preferred embodiments taken together with the drawings.

BRIEF DESCRIPTION OF THE DRAWINGS

The invention may take physical form in certain parts and arrangement of parts, preferred embodiments of which will be described in detail and illustrated in the accompanying drawings which form a part hereof and wherein.

DESCRIPTION OF THE PREFERRED EMBODIMENTS

Figure 1:
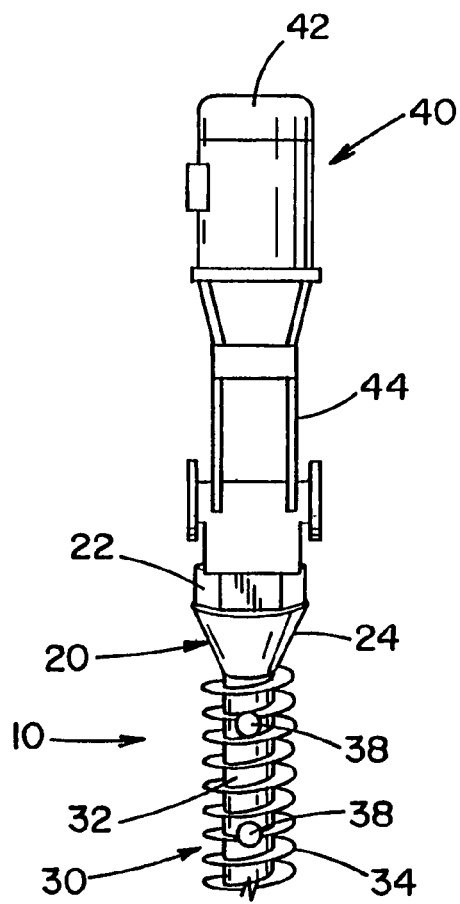
FIG. 1 is a partial perspective view of the front side prosthetic screw of the present invention which includes a pump mechanism connected to a top of the prosthetic screw.

Referring to the drawings, wherein the showings are for the purpose of illustrating the preferred embodiment of the invention only and not for the purpose of limiting same, FIGS. 1-11 illustrate an implant that is disclosed in United States Patent Publication No. 2004/0243130, which is incorporated herein. In particular, FIG. 1 illustrates a pedicle screw 10 for insertion into bone and/or cartilage of a vertebrae. The pedicle screw is described with particular reference for use with a surgical procedure involving the vertebrae; however, it will be appreciated that the pedicle screw can be used in other regions of a body (e.g., leg, arm, hand, foot, knee, hip, pelvis, rib cage, skull, etc.) to promote healing in such regions. It will also be appreciated that the bone screw system can be used in other areas of the vertebrae such as, but not limited to, the lamina, facets, etc. It will also be appreciated that the implant can be a form other than a pedicle screw.

Figure 2:
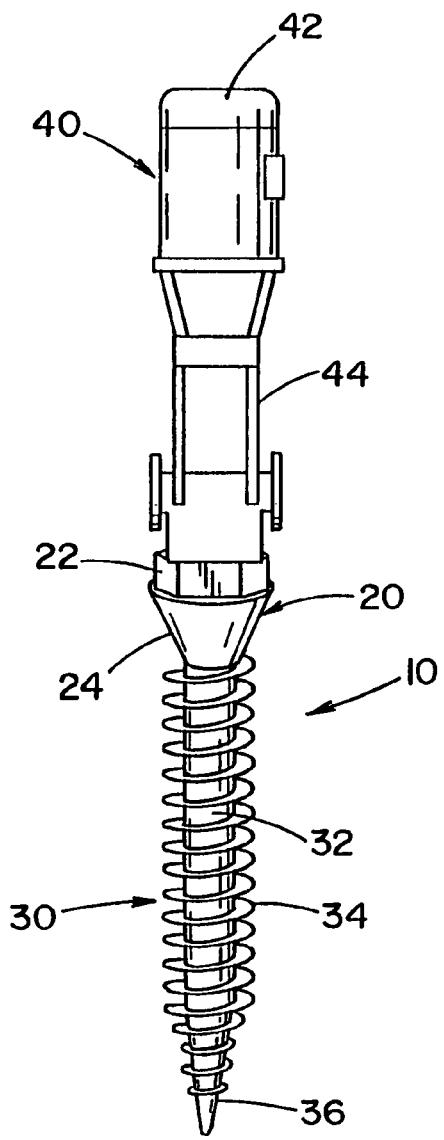
FIG. 2 is a perspective view of the back side of the prosthetic screw of FIG. 1.

Pedicle screw 10 is fabricated of a well known bio-compatible material such as stainless steel or titanium, and has a head 20 and a lower portion 30. The particular material or materials selected will generally depend on the location of the pedicle screw and the various objectives to be accomplished by the pedicle screw, as such, other or additional materials can be used. Head 20 has a hexagonal cross-sectional shaped top portion to facilitate in the insertion of the pedicle screw into the bone and/or cartilage. As can be appreciated, other shapes of the top portion can be used (e.g., octagonal, triangular, square, etc.). As can also be appreciated, the top portion 22 can include one or more indentations, slots, ridges, openings, etc. to facilitate in the insertion of the pedicle screw into the bone and/or cartilage. Positioned below the hexagonal top portion is a conical shaped portion 24 that terminates at the lower portion 30 of the pedicle screw. The lower portion of the pedicle screw includes an outer surface 32 that includes thread 34. The cross-sectional shape of the lower portion is substantially circular and has a substantially constant cross-sectional shape and cross-sectional area throughout the majority of the longitudinal length of the lower portion. The end 36 of the lower portion as illustrated in FIG. 2 tapers to a point; however, the end 36 can have a substantially flat configuration and/or have a non-tapering configuration. As can be appreciated, many other shapes and/or configurations of the head and/or lower portion can be used for the pedicle screw in the present invention.

In utilizing the pedicle screw, the pedicle screw is typically inserted into the bone and/or cartilage that includes a tapped or pre-drilled hole formed therein as a guide for the placement of the screw. The bone has a relatively hard compact shell, which encases a loose spongy cancellous bone material. The tap or pre-drilled hole facilitates in the insertion of the pedicle screw into the bone and/or minimizes damage to the bone during the insertion of the pedicle screw. Typically the tap or pre-drilled hole has a diameter that is less than the threads 34 on the lower portion 30 of the pedicle screw. For example, the tap or pre-drilled hole may have a diameter of about 8 mm, and the threads on the lower portion of the pedicle screw have a diameter of about 8.5 mm. The tap hole or pre-drilled hole forms a precise, preset path of insertion for the pedicle screw. Since the threads have a larger diameter than the opening in the bone and/or cartilage, the thread 34 bites into the bone and/or cartilage thereby accurately positioning the pedicle screw in the bone and/or cartilage and securing the pedicle screw in the bone and/or cartilage. Typically, the pedicle screw is adapted for use in securing a plate, rod and/or the like, not shown, from transitional or rotational motion.

Referring again to FIG. 1, a mechanical mechanism 40 is connected to top portion 22. The mechanical mechanism can be connected to the top portion in a variety of ways such as, but not limited to, screw, bolt, solder, weld, latch, snap, clip, etc. The connection can be designed to allow the mechanical mechanism to be at least partially connected to the top portion prior to, during, and/or after the pedicle screw has been inserted into the bone and/or cartilage. Alternatively, and/or additionally, the connection can be designed to allow the mechanical mechanism to be at least partially removably connected to the top portion of the pedicle screw. Still, alternatively, and/or additionally, the connection can be designed to be at least partially irremovably connected to one or more components of the mechanical mechanism to the top portion of the pedicle screw.

As illustrated in FIGS. 1 and 2, mechanical mechanism 40 includes a pump 42 and a cylinder 44 that is connected between pump 42 and top portion 22 of head 20. The pump can have any number of different configurations and/or can operate in any number of different ways. The pump is specifically designed to cause a substance contained in the cylinder to flow out of the cylinder. In one non-limiting configuration, the pump includes a piston that at least partially travels into the cylinder to cause one or more substances in the cylinder to flow out of the cylinder. The substance in the cylinder can include a variety of materials that promote bone and/or other tissue growth, inhibit rejection of the prosthetic implant, reduce infection, reduce inflammation, reduce pain, promote healing of surrounding tissue, function as a location and/or visual indicator, and/or the like.

Once the pedicle screw is connected to the bone and/or cartilage, the mechanical mechanism can be activated so that the pump causes one or more substances in the cylinder to flow out of the cylinder. The mechanical mechanism can alternatively be activated prior to complete insertion of the pedicle screw into the bone and/or cartilage. The activation of the mechanical mechanism can be manual and/or by a preprogrammed activation mechanism. The rate at which the pump causes one or more substances in the cylinder to flow out of the cylinder can be constant or manually and/or electronically regulated to vary over time.

Referring again to FIG. 1, the lower portion 30 of pedicle screw 10 includes two openings 38. As can be appreciated, more or less openings can be located in the lower portion. Furthermore, it can be appreciated that one or more openings can be located in the top portion of the pedicle screw. The openings are designed to allow at least a portion of the one or more substances in the cylinder 44 to flow out of the openings 38 and to the surrounding bone and/or cartilage. The top portion of the pedicle screw includes one or more openings, not shown, which allows the one or more substances from the cylinder 44 to flow into the one or more openings in the top portion and into one of more interior channels in the top portion, not shown. These one or more channels in the top portion allow the one or more substances to flow through the top portion and into one or more channels in the lower portion, not shown, and out through openings 38. The two or more openings can be positioned on the same side of the pedicle screw as illustrated in FIG. 1, or positioned in the lower portion in other manners.

Figure 3:
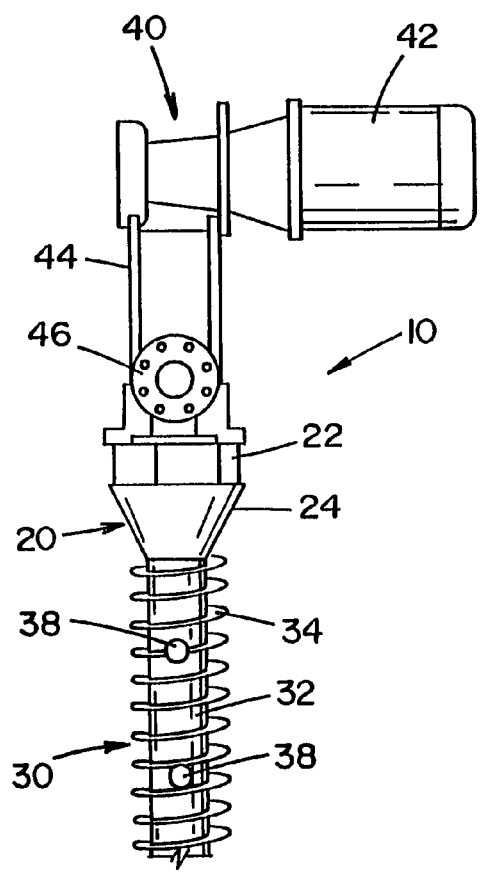
FIG. 3 is another partial perspective view of the front side prosthetic screw of the present invention which includes a pump mechanism connected to the top of the prosthetic screw wherein the pump is oriented in a different position on the prosthetic screw.
Figure 4:
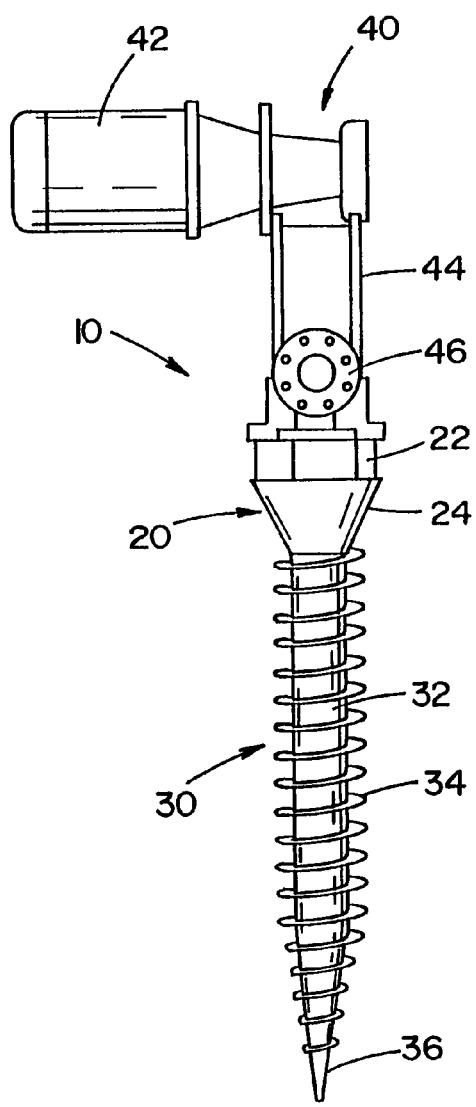
FIG. 4 is a perspective view of the back side of the prosthetic screw of FIG. 3.

As illustrated in FIGS. 3 and 4, mechanical mechanism 40 includes a pump or motor 42 and a cylinder 44 that are connected between pump or motor 42 and top section 22 of head 20. The pump or motor can have any number of different configurations and/or can operate in any number of different ways. The pump orientation illustrated in FIGS. 3 and 4 can facilitate in the use of this embodiment in regions of the spine wherein the orientation of the pump as illustrated in FIGS. 1 and 2 may interfere with the surrounding tissue. As can be appreciated, pump 42 can be orientated in a variety of other manners to facilitate the use of the pump and successful use of the pedicle screw. FIGS. 3 and 4 also illustrate a flange 46 positioned on cylinder 44. The flange 46 can be designed to allow one or more substances to be added to and/or removed from the cylinder prior to, during and/or after the pedicle screw is inserted into the bone and/or cartilage. The pump or motor can be designed to cause a substance contained in the cylinder to flow out of the cylinder, cause the head of the pedicle screw to move relative to the lower portion, cause the mechanical mechanism to move relative to the pedicle screw, cause the pedicle screw and/or mechanical mechanism to vibrate, etc. In one non-limiting configuration, the pump includes a piston that at least partially travels into the cylinder to cause one or more substances in the cylinder to flow out of the cylinder. The mechanical mechanism can be activated to cause one or more substances in the cylinder to flow out of the cylinder and/or to perform one or more other operations. The activation of the mechanical mechanism can be manual and/or by a preprogrammed activation mechanism. When the mechanical mechanism includes a pump, the rate at which the pump causes one or more substances in the cylinder to flow out of the cylinder can be constant or manually, and/or electronically regulated to vary over time. When the mechanical mechanism includes a motor to move one or more portions of the pedicle screw relative to one another, the rate at which the motor causes movement can be constant or manually, and/or electronically regulated to vary over time. As illustrated in FIG. 3, the lower portion 30 of pedicle screw 10 includes two openings 38. As can be appreciated, more or fewer openings can be located in the lower portion. Furthermore, it can be appreciated that one or more openings can be located in the head of the pedicle screw. The openings are designed to allow at least a portion of the one or more substances in the cylinder 44 to flow out of the openings 38 and to the surrounding bone and/or cartilage. The head of the pedicle screw can include one or more channels, not shown, which allows the one or more substances from the cylinder 44 to flow into the one or more channels in the head, not shown. As can be appreciated, the one or more channels in the head of the pedicle screw can be used to allow the one or more substances to flow through the head and into one or more channels in the lower portion, not shown, and out through openings 38. The two or more openings 38 can be positioned on the same side of the pedicle screw as illustrated in FIG. 3, or positioned in the lower portion in other manners. The mechanical mechanism is illustrated as oriented along the longitudinal axis of the pedicle screw. As can be appreciated, at least a portion of the mechanical mechanism can be arranged at one or more angles relative to the longitudinal axis of the pedicle screw (e.g., perpendicular, 30°, 45°, 60°, etc.).

Figure 5:
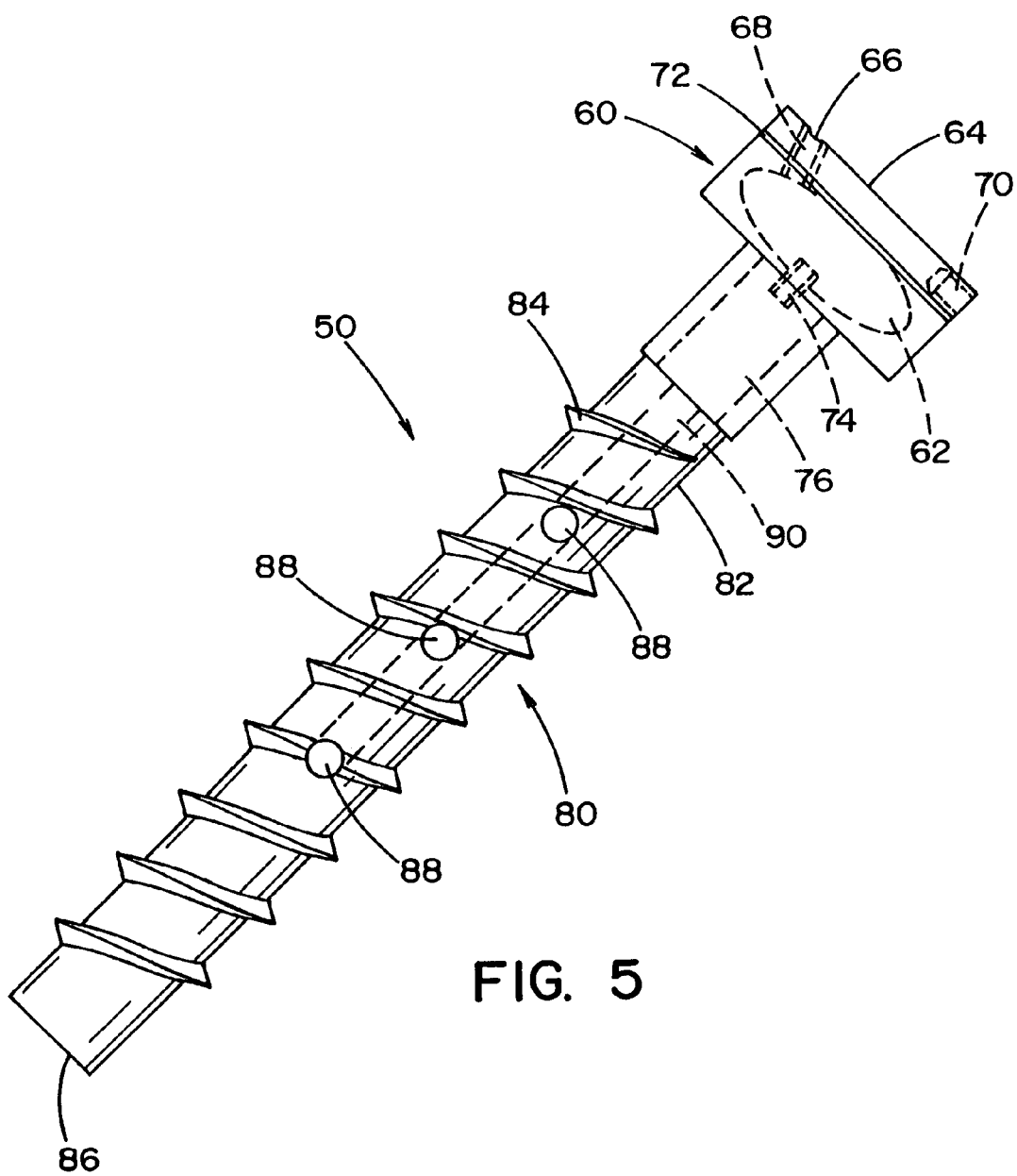
FIG. 5 is still another perspective view of the front side prosthetic screw of the present invention which includes a pump mechanism positioned in the top of the prosthetic screw.

Referring now to FIG. 5, pedicle screw 50 includes a head 60 and a lower portion 80. The cross-section of head 60 illustrates that the head-piece includes one or more reservoirs 62 for containing one or more substances described above. The reservoir is illustrated as having an ovoid shape; however, other shapes can be used. The top 64 of head 60 includes one or more port openings 66. Port opening 66 allows one or more substances to be inserted and/or removed from reservoir 62. One or more port passages 68 allows fluid passage between port opening 66 and reservoir 62. The port opening may have a sealing member to inhibit or prevent one or more substances in the reservoir from freely flowing out of the reservoir and out through port opening 66. One or more motors 70 are positioned in head 60. Motor 70 can be any type of motor that is small enough to be substantially fully positioned in the head. One non-limiting motor is a MEMS device. The head also includes one or more pressure plates 72 designed to be moved by motor 70 to thereby cause the one or more substances in reservoir 62 to flow out of the reservoir. One or more discharge ports 74 allow one or more substances to flow from the reservoir and into a base chamber 76 of head 60. As can be appreciated, motor 70 can be designed to perform other or additional functions (e.g., vibrations, moving one or more components relative to one another, etc.). The lower portion 80 of the pedicle screw includes an outer surface 82 that includes thread 84. The cross-sectional shape of the lower portion is substantially circular and has a substantially constant cross-sectional shape and cross-sectional area throughout the majority of the longitudinal length of the lower portion. The end 86 of the lower portion is substantially flat. As can be appreciated, many other shapes and/or configurations of the head and/or lower portion can be used for the pedicle screw (e.g., tapered end, etc.). The lower portion also includes three openings 88. As can be appreciated, more or fewer openings can be located in the lower portion (e.g., opening in the end, etc.). The openings are designed to allow at least a portion of the one or more substances to flow out of the openings 88 and to the surrounding bone and/or cartilage. The lower portion also includes one or more channels 90 to allow the one or more substances to flow from base chamber 76 of head 60 and out through openings 88. The two or more openings can be positioned on the same side of the pedicle screw as illustrated in FIG. 5, or be positioned in other locations. The mechanical mechanism is designed to be fully or partially embedded under the skin after completion of a surgical procedure. The mechanical mechanism can be designed to be permanently left in the body, or be removed from the body after performing its function. As stated above, once the pedicle screw is connected to the bone and/or cartilage, the mechanical mechanism can be activated so that the pump causes one or more substances to flow out of openings 88. The mechanical mechanism can alternatively be activated prior to complete insertion of the pedicle screw into the bone and/or cartilage. The activation of the mechanical mechanism can be manual and/or by a preprogrammed activation mechanism. The rate at which the pump causes one or more substances in the cylinder to flow out of the cylinder can be constant or be manually and/or electronically regulated to vary over time.

Figure 6:
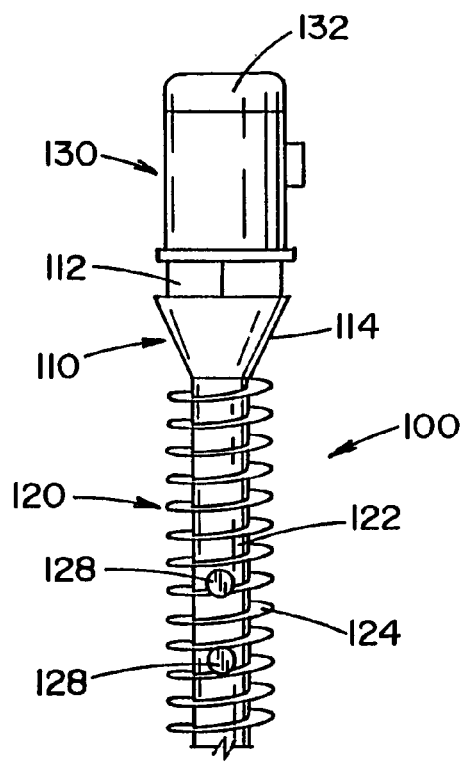
FIG. 6 is a partial perspective view of the front side prosthetic screw of the present invention which includes an electrical mechanism connected to the top of the prosthetic screw.
Figure 7:
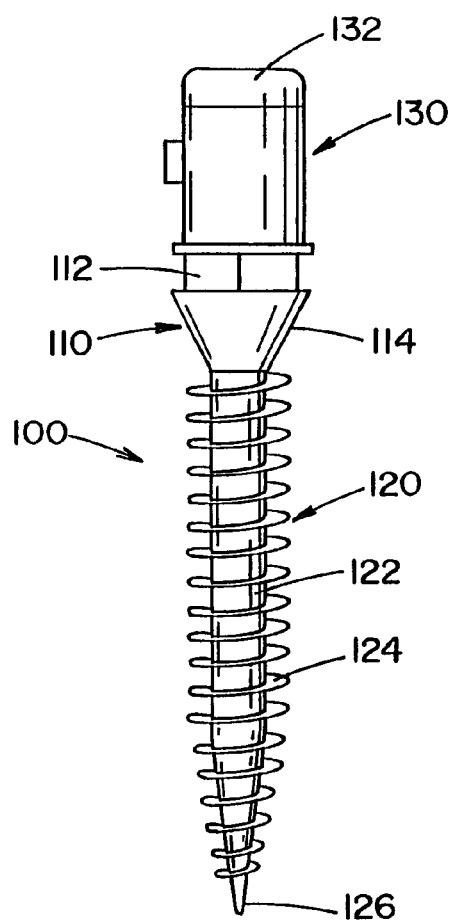
FIG. 7 is a perspective view of the back side of the prosthetic screw of FIG. 6.

Referring now to FIGS. 6 and 7, pedicle screw 100 includes a head 110 and a lower portion 120. Head 110 has a hexagonal cross-sectional shaped top section 112 to facilitate in the insertion of the pedicle screw into the pedicle. As can be appreciated, other shapes of the top section can be used. As can also be appreciated, the top section 112 can include one or more indentations, slots, ridges, openings, etc. to facilitate in the insertion of the pedicle screw into the pedicle. Positioned below the hexagonal top section is a conical shaped portion 114 that terminates at the lower portion 120 of the pedicle screw. The lower portion of the pedicle screw includes an outer surface 122 that includes thread 124. The cross-sectional shape of the lower portion is substantially circular and has a substantially constant cross-sectional shape and cross-sectional area throughout the majority of the longitudinal length of the lower portion. The end 126 of the lower portion as illustrated in FIG. 7 tapers to a point; however, the end 126 can have a substantially flat configuration and/or have a non-tapering configuration. As can be appreciated, many other shapes and/or configurations of the head and/or lower portion can be used for the pedicle screw in the present invention. A head 130 in the form of an electrical mechanism 130 is connected to top section 112 of head 110, The head is threaded onto the head of the pedicle screw; however, the head-piece can be connected to the pedicle screw in other or additional means (e.g., screw, bolt, solder, weld, latch, snap, clip, etc.). The head can be at least partially connected to and/or removed from the pedicle screw prior to, during, and/or after the pedicle screw has been inserted into the pedicle. The electrical mechanism can include a battery or electric generator 132. The battery or electric generator can have any number of different configurations and/or can operate in any number of different ways. The battery or electric generator can be designed to supply an electric current to one or more surfaces of the pedicle screw. In one non-limiting configuration, the electrical mechanism includes a battery to supply electric current to one or more regions on the pedicle screw. Once the pedicle screw is connected to the bone and/or cartilage, the electrical mechanism can be activated so that the battery or electric generator begins supplying electric currents to one or more regions on the pedicle screw. The electrical mechanism can alternatively be activated prior to complete insertion of the pedicle screw into the bone and/or cartilage. The activation of the electrical mechanism can be manual and/or by a preprogrammed activation mechanism. The time period, current level and/or voltage level at which the electrical mechanism discharges electric current can be constant or manual, and/or electronically regulated to vary over time. The lower portion 120 of pedicle screw 100 includes two electrodes 128. As can be appreciated, additional electrodes can be located in the lower portion. Furthermore, it can be appreciated that one or more electrodes can be located in the head of the pedicle screw. The electrodes are designed to conduct electrical current about the surrounding bone and/or cartilage. The head of the pedicle screw includes one or more regions, not shown, which allow current to be conducted between the battery or electric generator and the two or more electrodes in the lower portion. For example, the one or more regions can be a passageway for containing and electrically conducting material such as, but not limited to, a wire. The two or more electrodes can be positioned on the same side of the pedicle screw as illustrated in FIG. 6, or be positioned in the lower portion in other manners. The electrical mechanism is designed to be fully or partially embedded under the skin after completion of a surgical procedure. The electrical mechanism can be designed to be permanently left in the body, or be removed from the body after performing its function.

Figure 8:
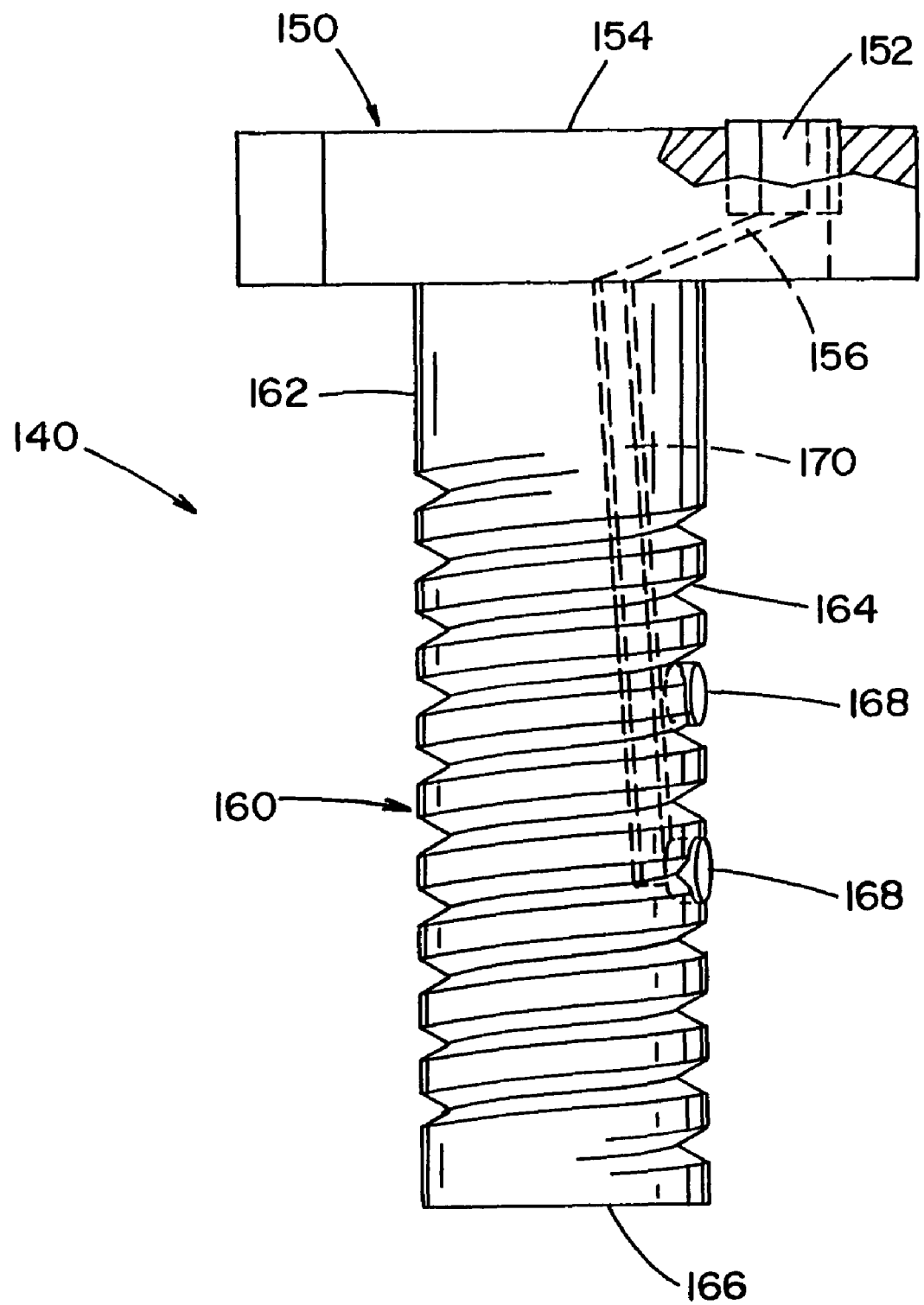
FIG. 8 is still another perspective view of the front side of the prosthetic screw of the present invention which includes an electrical mechanism positioned in the top of the prosthetic screw.

Referring now to FIG. 8, pedicle screw 140 includes a head 150 and a lower portion 160. The cross-section of head 150 illustrates that the head includes a battery 152 positioned in top surface 154. The battery is illustrated as having a cubical shape; however, other shapes can be used. The head has a rectangular shape; however, other shapes can be used. The battery can be connected in the head in a variety of manners. The battery can also be connected such that the battery can be periodically replaced. A channel 156 is positioned under the battery and travels between the battery and lower portion 160 of the pedicle screw. Typically, a wire or other electrical conductor is positioned in the channel. The discharge rate, the discharge duration, etc., of the battery can be constant or electronically controlled.

The lower portion 160 of the pedicle screw includes an outer surface 162 that includes thread 164. The cross-sectional shape of the lower portion is substantially circular and has a substantially constant cross-sectional shape and cross-sectional area throughout the majority of the longitudinal length of the lower portion. The end 166 of the lower portion is substantially flat. As can be appreciated, many other shapes and/or configurations of the head and/or lower portion can be used for the pedicle screw. The lower portion also includes two electrodes 168. As can be appreciated, more electrodes can be located in the lower portion. Furthermore, it can be appreciated that one or more electrodes can be located in the top portion of the pedicle screw. The electrodes are designed to conduct current between the electrodes and to the surrounding tissue. The lower portion also includes one or more channels 170 wherein an electrical conductor is positioned. Channel 170 enables an electrical conductor to connect the electrodes 168 to the electrical conductor in channel 156. The electrodes can be positioned on the same side of the pedicle screw as illustrated in FIG. 8, or positioned on the lower portion in other manners. Once the pedicle screw is connected to the bone and/or cartilage, the electrical mechanism can be activated so that the battery conducts a current between the electrodes. The electrical mechanism alternatively, can be activated prior to complete insertion of the pedicle screw into the bone and/or cartilage. The activation of the electrical mechanism can be manual and/or by a preprogrammed activation mechanism. The discharge rate at which the battery conducts current between the electrodes can be constant or manual and/or electronically regulated to vary over time.

Figure 9:
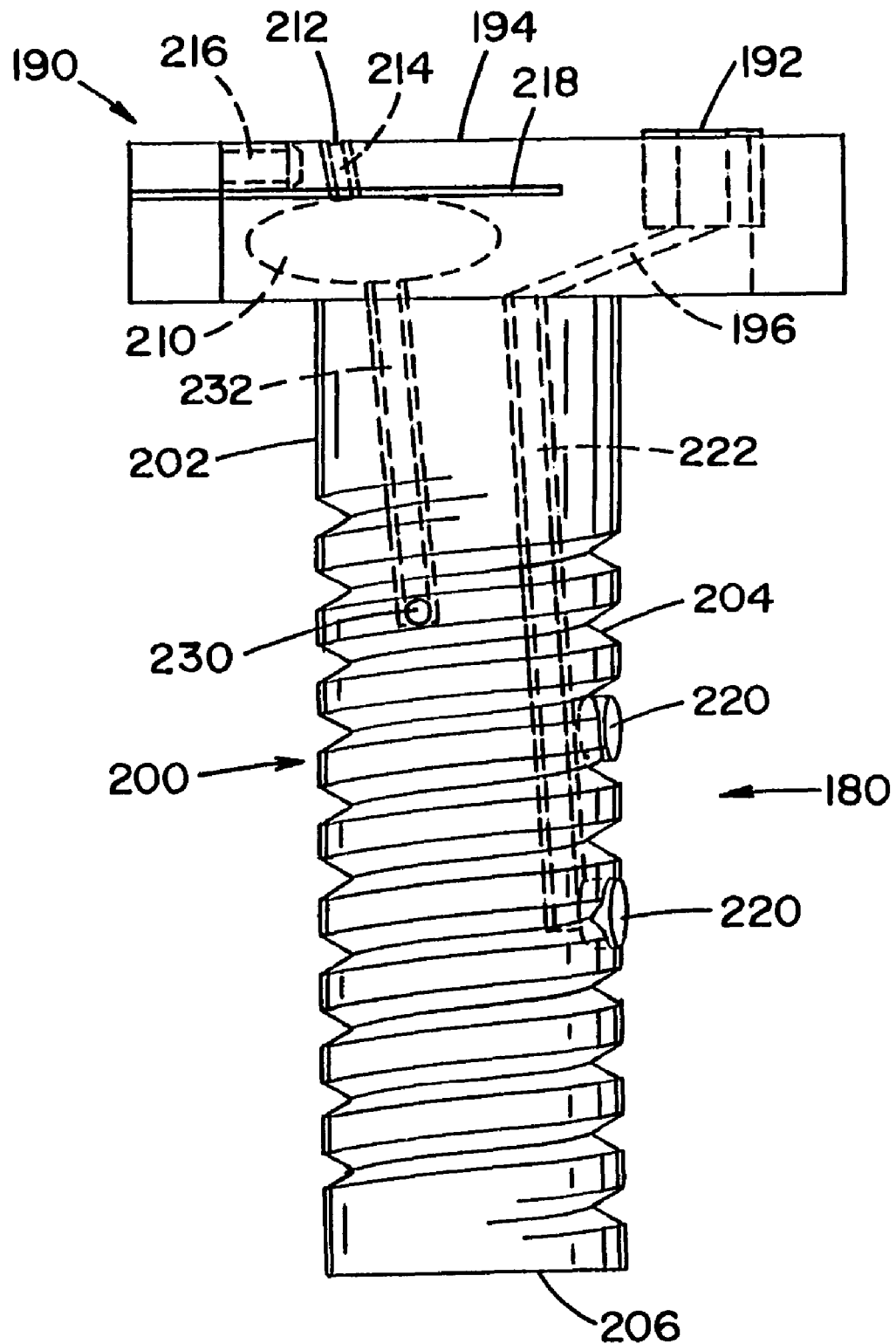
FIG. 9 is yet another perspective view of the front side of the prosthetic screw of the present invention which includes an electrical mechanism and a pump mechanism positioned in the top of the prosthetic screw.
Figure 10:
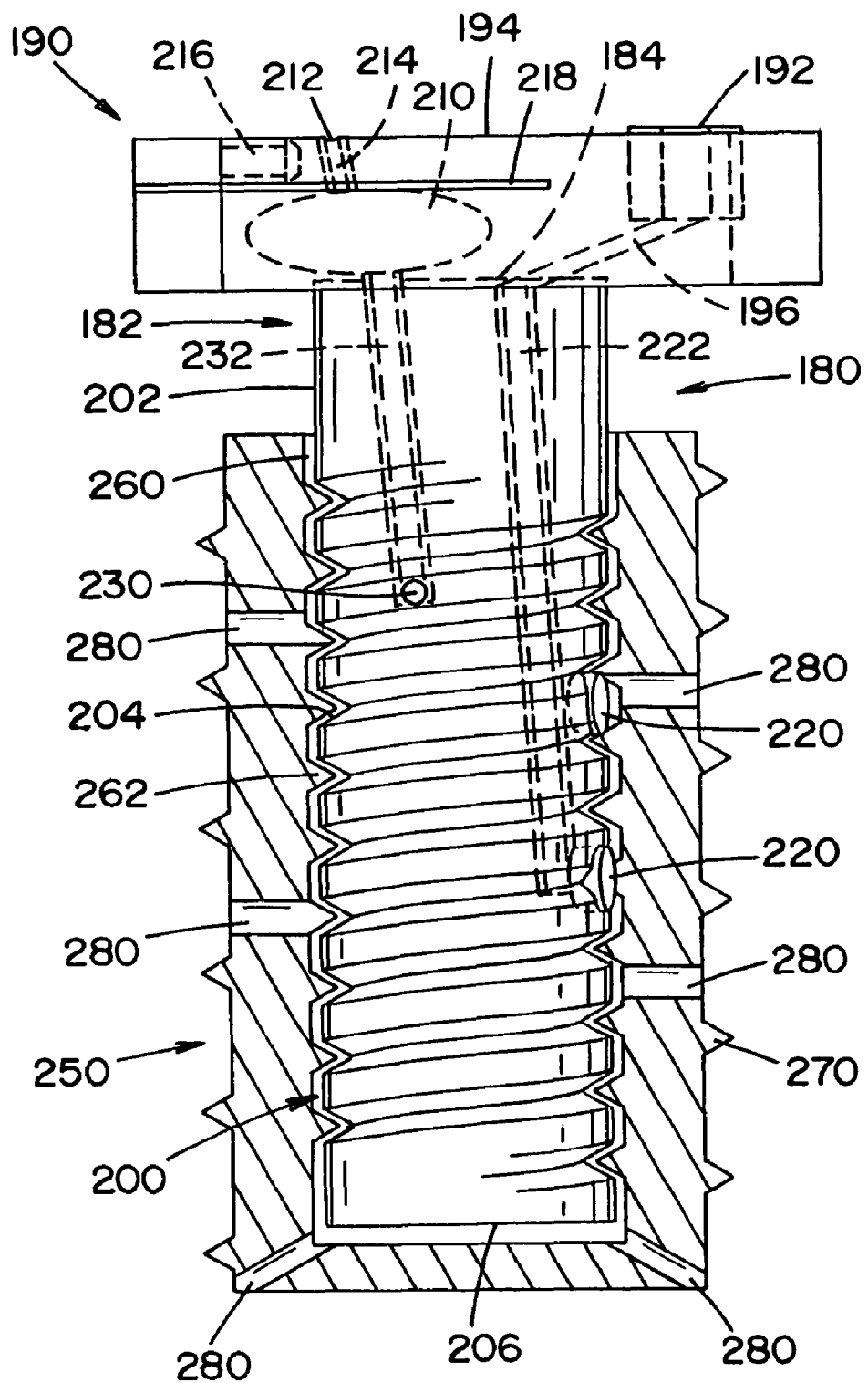
FIG. 10 is a perspective view of the front side of the prosthetic screw that is shown in a cut away portion of a sleeve.

Referring now to FIG. 9, pedicle screw 180 includes a head 190 and a lower portion 200. Head 190 includes a battery 192 positioned in top surface 194. The battery configuration is similar to that of FIG. 8. As explained with respect to the pedicle screw in FIG. 8, the battery can be connected in the head in a variety of manners. The battery can also be connected such that the battery can be periodically replaced. A channel 196 is positioned under the battery and travels between the battery and lower portion 200 of the pedicle screw. Typically a wire or other electrical conductor is positioned in the channel. The discharge rate, the discharge duration, etc. of the battery can be constant or electronically controlled. Head 190 also includes one or more reservoirs 210 for containing one or more substances described above. The reservoir is illustrated as having an ovoid shape; however, as explained with respect to FIG. 5, other shapes can be used. The top of head 190 includes one or more port openings 212 to allow one or more substances to be inserted and/or removed from the reservoir. One or more port passages 214 allows fluid passage between port opening 212 and reservoir 210. The port opening can be designed similar to the port opening described with respect to FIG. 5. One or more motors 216 are positioned in head 190. The motor design, type and configuration can be similar to the motor disclosed in FIG. 5. The head also includes one or more pressure plates 218 designed to be moved by the motor to cause the one or more substances in the reservoir to flow out of the reservoir. One or more discharge ports 220 allow one or more substances to flow from the reservoir. The lower portion 200 of the pedicle screw includes an outer surface 202 that includes thread 204. The cross-sectional shape of the lower portion is substantially circular and has a substantially constant cross-sectional shape and cross-sectional area throughout the majority of the longitudinal length of the lower portion. The end 206 of the lower portion is substantially flat. As can be appreciated, many other shapes and/or configurations of the head and/or lower portion can be used for the pedicle screw. The lower portion also includes two electrodes 220. As can be appreciated, more electrodes can be located in the lower portion. Furthermore, it can be appreciated that one or more electrodes can be located in the head of the pedicle screw. The electrodes are designed to conduct current between the electrodes and the bone and/or surrounding tissue. The lower portion also includes one or more channels 222 wherein an electrical conductor is positioned. Channel 222 enables an electrical conductor to connect the electrodes 220 to the electrical conductor in channel 196. The electrodes can be positioned on the same side of the pedicle screw as illustrated in FIG. 8, or positioned on the lower portion in other manners. The lower portion 200 of the pedicle screw also includes an opening 230. As can be appreciated, more openings can be located in the lower portion. Furthermore, it can be appreciated that one or more openings can be located in the head of the pedicle screw. The opening is designed to allow at least a portion of the one or more substances to flow out of the opening and to the surrounding bone and/or cartilage. The lower portion also includes one or more channels 232 to allow the one or more substances to flow from the reservoir and out through opening 230. The operation of the motor to cause the one or more substances to flow out through opening 230 can be similar to the manner discussed with respect to FIG. 5. Once the pedicle screw is connected to the bone and/or cartilage, the electrical mechanism can be activated so that the battery conducts a current between the electrodes. The electrical mechanism alternatively can be activated prior to complete insertion of the pedicle screw into the bone and/or cartilage. The activation of the electrical mechanism can be manual and/or by a prepogramed activation mechanism. The discharge rate at which the battery conducts current between the electrodes can be constant or be manually and/or electronically regulated to vary over time. Furthermore, the mechanical mechanism can be activated to cause one or more substances in the cylinder to flow out of the cylinder and/or to perform one or more other operations. The activation of the mechanical mechanism can be manual and/or by a preprogrammed activation mechanism. When the mechanical mechanism includes a pump, the rate at which the pump causes one or more substances in the cylinder to flow out of the cylinder can be constant or manual and/or electronically regulated to vary over time. When the mechanical mechanism includes a motor to move one or more portions of the pedicle screw relative to one another, the rate at which the motor causes movement can be constant or manual and/or electronically regulated, to vary over time.

The pedicle screw can be at least partially coated with and contain in one or more cavities a substance that includes one or more materials that promote bone and/or other tissue growth, inhibit rejection of the prosthetic implant, reduce infection, reduce inflammation, reduce pain, promote healing of surrounding tissue, function as a location and/or visual indicator, and/or the like.

As stated above, once the pedicle screw is connected to the bone and/or cartilage, the electrical mechanism can be activated so that the battery conducts a current between the electrodes. The electrical mechanism alternatively can be activated prior to complete insertion of the pedicle screw into the bone and/or cartilage. The activation of the electrical mechanism can be manual and/or by a preprogrammed activation mechanism. The discharge rate at which the battery conducts current between the electrodes can be constant or be manually and/or electronically regulated to vary over time.

Figure 11:
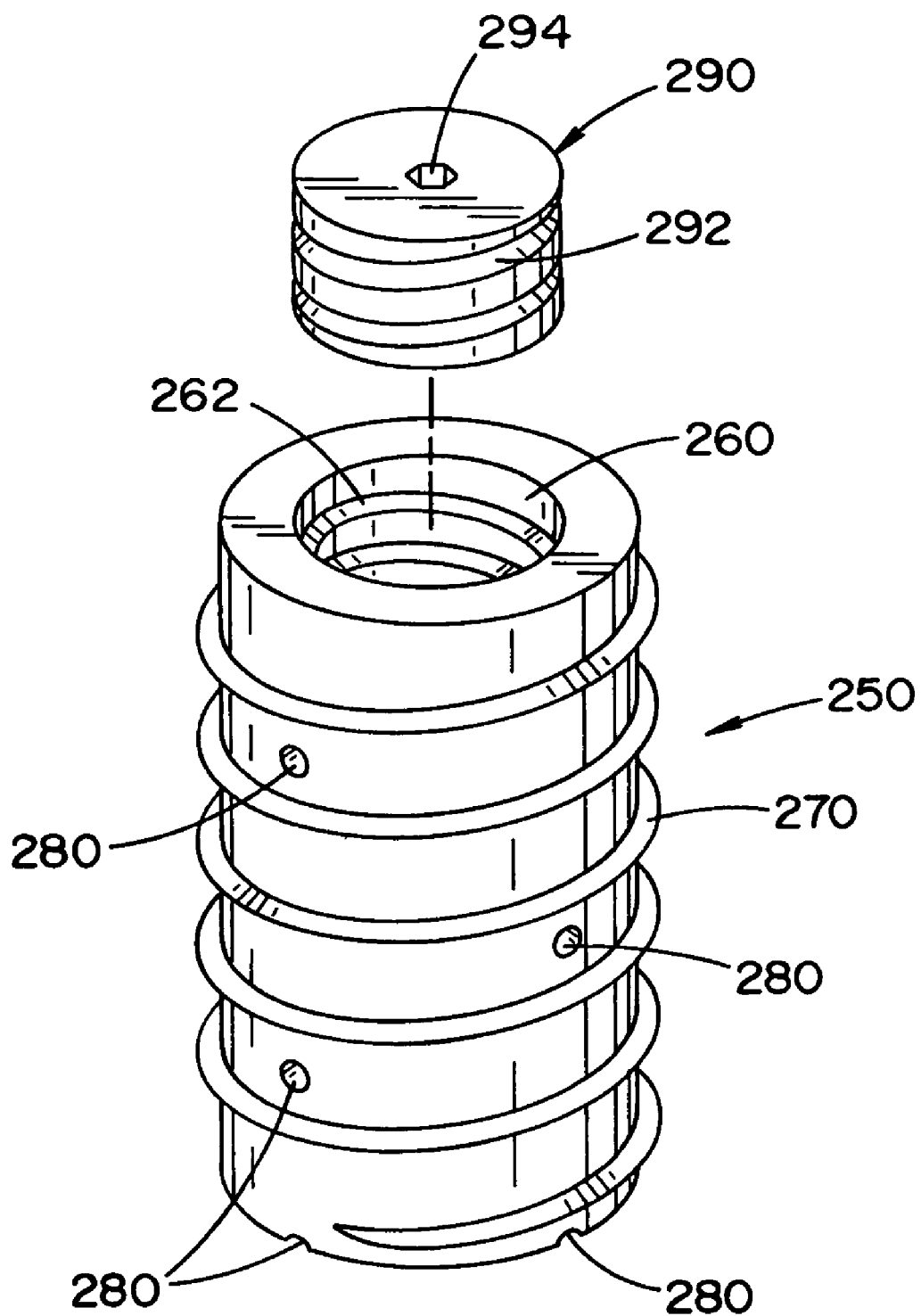
FIG. 11 is perspective view of the front side of the sleeve shown in FIG. 10.
Figure 12:
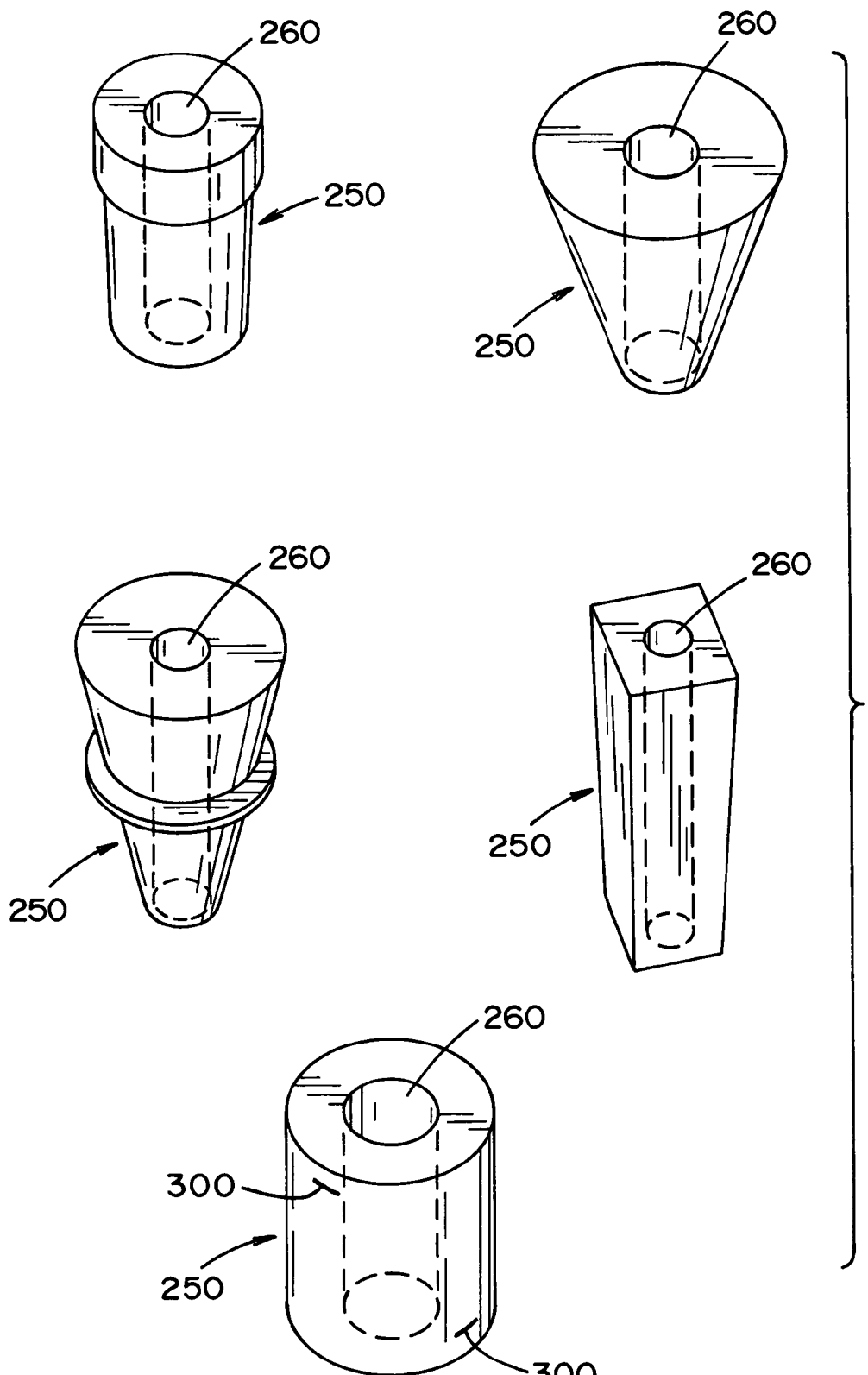
FIG. 12 is a pictorial view of several possible shapes of a sleeve.

Referring now to FIGS. 10-13, there is illustrated the pedicle screw of FIG. 9 inserted in a sleeve 250. Sleeve 250 without the pedicle screw is illustrated in FIG. 11. The sleeve is illustrated as having a substantially uniform circular cross-sectional shape; however, it can be appreciated that other shapes can be used. Several additional shapes of the sleeve are illustrated in FIG. 12. As can be appreciated, the sleeve can have many other shapes. The sleeve includes a central cavity 260 that is designed to receive pedicle screw 180. The central cavity is illustrated as passing through the full longitudinal length of the sleeve; however, this is not required. The central cavity is illustrated as having a uniform cross-sectional shape; however, this is not required. The central cavity can include threads 262 designed to engage thread 204 on lower portion 200 of pedicle screw 180; however, the cavity can include a smooth surface or have other types of non-smooth surfaces. The threads in the central cavity and on the pedicle screw enable the pedicle screw to be threaded into and/or removed from the sleeve. As can be appreciated, other and/or additional mechanisms can be used to facilitate in securing the pedicle screw in the sleeve. Sleeve 250 is illustrated as including a threaded outer surface 270. Threads 270 are designed to facilitate in anchoring the sleeve in an opening in the bone. As can be appreciated, the outer surface can have other and/or additional surface configurations to facilitate in anchoring the sleeve in an opening in the bone. As can also be appreciated, the outer surface can be smooth. Sleeve 250 is also illustrated as including several openings 280. Openings 280 are designed to enable fluids to flow into and/or out of the interior of sleeve 250; however, such openings are not required. For instance, when the pedicle screw is designed to inject and/or secrete one or more substances into and/or about the bone, the one or more openings in the sleeve can allow the one or more substances to flow out of the sleeve. Openings 280 can alternatively or additionally be used to enable tissue and/or bone to secure to the sleeve so as to facilitate in anchoring the sleeve in an opening in the bone. The openings can also be used to facilitate in the exposure of the surrounding tissue to electrical stimulation by the pedicle screw when the pedicle screw is designed to discharge such electro-stimulation. A cap 290 can be used in conjunction with the sleeve. The cap includes threads 292 that are designed to be threaded onto threads 262 in central cavity 260. As can be appreciated, the cap can be designed to connect to the sleeve in other or additional ways. The cap also includes an opening 294 that is used to insert and/or remove the cap from the sleeve; however, this is not required. As can be appreciated, the cap can include other or additional structures that is used to insert and/or remove the cap from the sleeve. The outer surface of the cap and/or sleeve can include and/or be coated with one or more substances to facilitate in the success of the sleeve and/or pedicle screw. The sleeve can include one or more markers 300 that can be used to locate the position of the sleeve in the bone and/or cartilage; however, this is not required.

Figure 13:
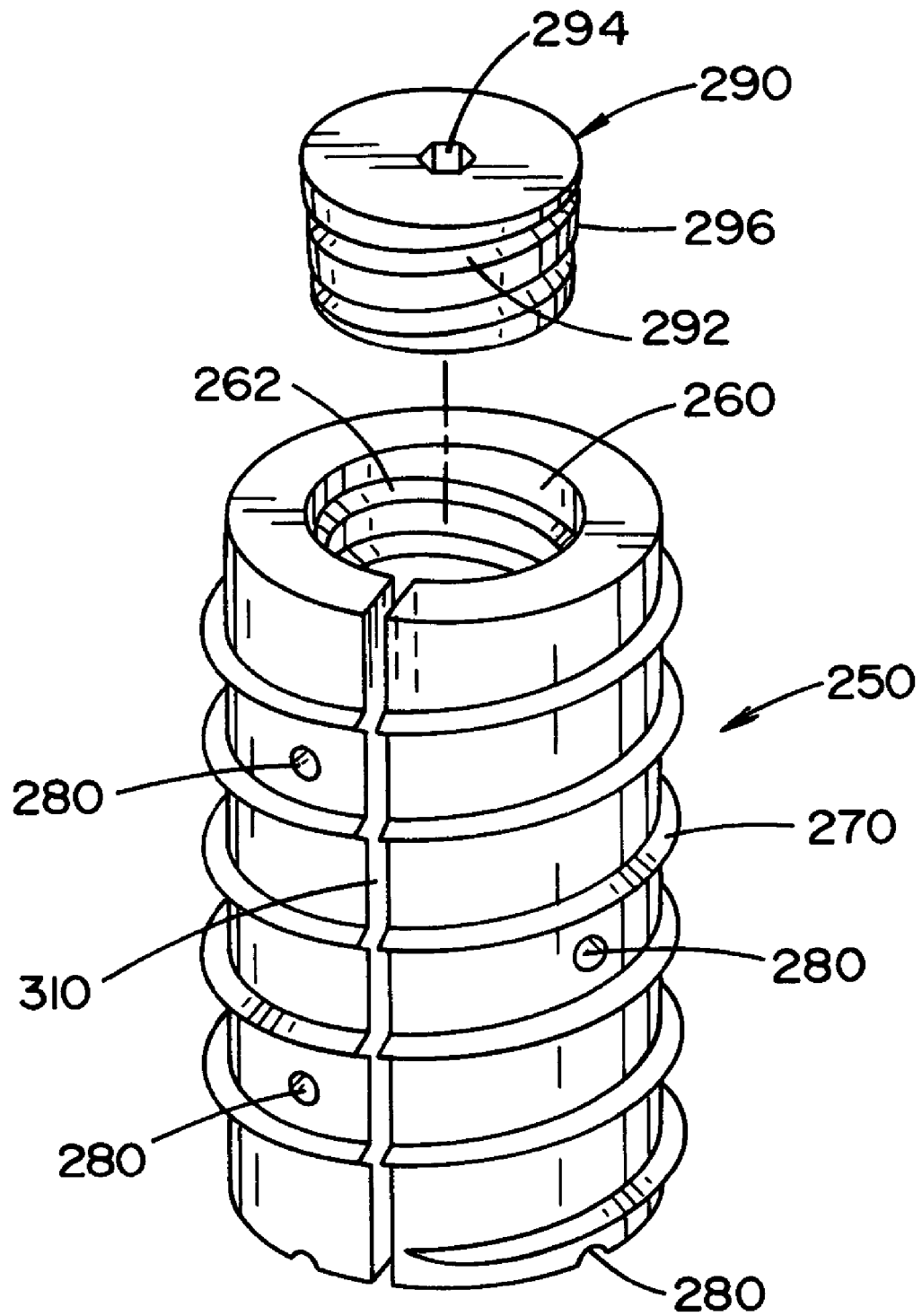
FIG. 13 is perspective view of the front side of a modification of the sleeve shown in FIG. 11.

Referring now to FIG. 13, there is illustrated a sleeve 250 having a similar configuration as the sleeve shown in FIG. 11. Sleeve 250 includes a side slot 310 that extends partially along the longitudinal length of the sleeve. Cap 290 is illustrated as having a tapered side wall 296. When cap 290 is inserted into cavity 260 of sleeve 250, the cap causes side slot to slightly enlarge and thereby enlarge the cross-sectional area of the sleeve. The enlargement of the cross-sectional area of the sleeve enables the sleeve to be set and/or secured in the opening or hole of the bone and/or cartilage. As can be appreciated, the lower portion 30 of pedicle screw 10 can also include a tapered portion that causes enlargement of the cross-sectional area of the sleeve; however, this is not required, as can be appreciated, devices other than cap 290 and/or pedicle screw 10 can be used to cause enlargement of the cross-sectional area of the sleeve. Sleeve 250 can also be designed such that the side slot causes a reduction in the cross-sectional area of the sleeve so as to facilitate in the removal of the sleeve from the bone and/or cartilage; however, this is not required.

The use of the sleeve can facilitate in various types of medical procedures. For instance, the sleeve can be used to enable easier extraction and/or replacement of the pedicle screw in a bone. In this procedure, the pedicle screw may to designed to secrete various substances and/or perform one or more types of electro-stimulation. Over a period of time the pedicle screw may need to be replaced so as to replenish the pedicle screw with additional substances and/or replace the pedicle screw having a replenished supply of one or more substances. Alternatively, and/or additionally, the pedicle screw may need to be replaced so as to recharge the pedicle screw with further electro-stimulation treatments and/or replace the pedicle screw having a new power supply. Alternatively, the use of the pedicle screw may be completed and needs to be removed from the bone. In these situations, the sleeve facilitates in the removal and/or replacement of the pedicle screw in the bone.

The simplicity of the insertion and/or removal of the pedicle screw from the sleeve can lend such procedure to outpatient or day surgery (e.g., doctor's office, ambulatory surgery center, etc.). The procedure could be designed to merely involve minor micro-invasive surgery. As a result, the use of the sleeve could reduce the cost to the patient and much of the inconvenience to the patient.

The sleeve could be inserted in a patient by forming an opening in the bone and then inserting the sleeve in the opening. The sleeve can then be left in the bone for a sufficient period of time until the sleeve is properly anchored to and/or set in the bone. This initial procedure could lend itself to being performed by outpatient or day surgery in a doctor's office, ambulatory surgery center, etc. This minor micro-invasive surgery could be performed in a shorter time and at a lower cost than in a hospital for an extended stay. Once again, this procedure could also lend itself to being performed by outpatient or day surgery in a doctor's office, ambulatory surgery center, etc.

When the sleeve is inserted on the bone and allowed to set and/or anchor to the bone prior to inserting the pedicle screw in the bone, a cap 290 can be used at the end of the sleeve to at least partially inhibit bone or tissue from growing in the top of the sleeve, which growth could interfere with the later insertion of the pedicle screw. At the time the pedicle screw is to be inserted in the sleeve, the cap 290 is removed from the sleeve and the pedicle screw is then inserted into the sleeve. As can be appreciated, if the pedicle screw is to be inserted in the sleeve shortly after the sleeve is inserted in the opening in the bone, the use of the cap can be eliminated; however, this is not required.

As can also be appreciated, the sleeve and pedicle screw can be inserted simultaneously into an opening in the bone and/or cartilage.

As can further be appreciated, the insertion of the sleeve may be performed by outpatient or day surgery in a doctor's office, ambulatory surgery center, etc., and the insertion of the pedicle screw can be inserted by some extended surgical procedure in a hospital, especially if the insertion of the pedicle involves a more complex procedure and/or is part of some larger procedure (e.g., the insertion of a stabilizing system, etc.).

The invention has been described with reference to the preferred embodiments. These and other modifications of the preferred embodiments as well as other embodiments of the invention will be obvious from the disclosure herein, whereby the foregoing descriptive matter is to be interpreted merely as illustrative of the invention and not as a limitation. It is intended to include all such modifications and alterations insofar as they come within the scope of the appended claims.

We claim:

1. A method of at least partially inserting an implant into a bone and/or cartilage of a spine comprising:
    a) selecting an implant, said implant including a head and a lower portion connected to the head;
    b) selecting a sleeve that includes a side wall, a top wall, a bottom wall, a cavity and a removable cap in said opening in said top wall, said top wall having an opening into said cavity, said cavity designed to at least partially telescopically receive said lower portion of said implant;
    c) forming an opening in said bone and/or cartilage of said spine;
    d) at least partially inserting said sleeve into said opening;
    e) allowing a period of time to pass after said sleeve is inserted in said opening in said bone and/or cartilage and prior to said lower portion of said implant being at least partially inserted and secured into said cavity of said sleeve;
    f) removing said cap from said top opening after passage of said period of time, said period of time enabling said sleeve to at least partially set in said opening in said bone and at least partially allow bone to grow about said sleeve before said lower portion of said implant is at least partially inserted and secured into said cavity of said sleeve; and,
    g) at least partially inserting and securing said lower portion of said implant into said cavity of said sleeve.

2. The method as defined in claim 1, including the step of inserting a) at least one medicine, b) at least one biological agent, or a) and b) in said cavity prior to inserting said cap on said opening in said top wall.

3. The method as defined in claim 1, wherein said sleeve includes a plurality of openings in said side wall, and including the step of enabling at least one medicine, biological agent, or combinations thereof to pass through at least one of said openings in said side wall and to facilitate in the healing of the bone and/or cartilage, growth of the bone and/or cartilage, or combinations thereof at least partially about said sleeve.

4. The method as defined in claim 3, including the step of inserting a) at least one medicine, b) at least one biological agent, or a) and b) in said cavity prior to inserting said cap on said opening in said top wall.

5. The method as defined in claim 4, including the step of inserting a) at least one medicine, b) at least one biological agent, or a) and b) in said cavity prior to said implant being inserted in said cavity.

6. The method as defined in claim 4, wherein said sleeve includes at least one engagement member on an outer surface of said side wall, said engagement member designed to promote a rigid connection between said sleeve and said bone and/or cartilage.

7. The method as defined in claim 4, wherein said sleeve includes at least one engagement member in said cavity, said engagement member designed to engage and secure said implant in said cavity.

8. The method as defined in claim 4, wherein said side wall of said sleeve includes a side slot that extends partially along the longitudinal length of said side wall.

9. The method as defined in claim 3, including the step of simultaneously inserting said sleeve and said implant in said bone and/or cartilage, said lower portion of said implant at least partially inserted in said cavity of said sleeve prior to said sleeve being inserted in said bone and/or cartilage.

10. The method as defined in claim 9, wherein said sleeve includes at least one engagement member on an outer surface of said side wall, said engagement member designed to promote a rigid connection between said sleeve and said bone and/or cartilage.

11. The method as defined in claim 9, wherein said sleeve includes at least one engagement member in said cavity, said engagement member designed to engage and secure said implant in said cavity.

12. The method as defined in claim 9, wherein said side wall of said sleeve includes a side slot that extends partially along the longitudinal length of said side wall.

13. The method as defined in claim 3, wherein said sleeve includes at least one engagement member on an outer surface of said side wall, said engagement member designed to promote a rigid connection between said sleeve and said bone and/or cartilage.

14. The method as defined in claim 13, wherein said side wall of said sleeve includes a side slot that extends partially along the longitudinal length of said side wall.

15. The method as defined in claim 3, wherein said sleeve includes at least one engagement member in said cavity, said engagement member designed to engage and secure said implant in said cavity.

16. The method as defined in claim 3, wherein said side wall of said sleeve includes a side slot that extends partially along the longitudinal length of said side wall.

17. The method as defined in claim 1, wherein said sleeve has a three dimensional shape, said three dimensional shape selected from the group consisting of spherical shape, pyramid-shaped, cube-shaped, prism-shaped, egg-shaped, parallelepiped-shaped, and conical-shaped.

18. A method of connecting an implant to a bone or cartilage of a spine comprising:
  a) selecting an implant, said implant including a head and a lower portion connected to the head, said head including at least one arrangement selected from a group consisting of a) connector to connect to a support structure used for a spine, b) a current generating device that directs current from the implant to the bone or cartilage of the spine, and c) a pump device that directs fluid from the implant to the bone or cartilage of the spine;
  b) selecting a sleeve that includes a side wall, a top wall, a bottom wall and a cavity, said top wall having an opening into said cavity, said cavity designed to at least partially telescopically receive said lower portion of said implant, said cavity including a connection arrangement to secure said implant to said sleeve;
  c) forming an opening in said bone or cartilage of said spine;
  d) inserting said bottom wall and at least a portion of said side wall of said sleeve into said opening, said step of inserting said sleeve into said opening of said bone or cartilage includes a) placing said bottom wall of said sleeve at the top of said opening in said bone or cartilage, b) moving a medical instrument into contact with said top wall of said sleeve, c) rotating said sleeve by said medical instrument to cause said side wall of said sleeve to be at least partially inserted in said opening of said bone or cartilage, and d) removing a cap from said top wall of said sleeve after said side wall of said sleeve to be at least partially inserted in said opening of said bone or cartilage, said cap designed to cover said opening into said cavity while said sleeve is at least partially inserted in said opening of said bone or cartilage;
  e) securing said sleeve to said bone and/or cartilage of said spine; and,
  f) inserting at least a portion of said lower portion of said implant into said cavity of said sleeve and securing said implant to said sleeve.

19. The method as defined in claim 18, wherein an outer surface of said outer wall of said sleeve includes a thread, said thread designed to facilitate in the connection between said sleeve and said bone or cartilage.

20. The method as defined in claim 18, wherein said side wall of said sleeve includes a side slot that extends at least partially along the longitudinal length of said side wall, said side slot designed to enable said sleeve to change a cross-sectional area of said sleeve as said sleeve is inserted into said opening of said bone or cartilage.

21. The method as defined in claim 18, wherein said sleeve has a three dimensional shape, said three dimensional shape selected from the group consisting of spherical shape, pyramid-shaped, cube-shaped, prism-shaped, egg-shaped, parallelepiped-shaped, and conical-shaped.

22. A method of connecting an implant to a bone or cartilage of a spine comprising:
  a) selecting an implant, said implant including a head and a lower portion connected to the head, said head including at least one arrangement selected from a group consisting of a) connector to connect to a support structure used for a spine, b) a current generating device that directs current from the implant to the bone or cartilage of the spine, and c) a pump device that directs fluid from the implant to the bone or cartilage of the spine;
  b) selecting a sleeve that includes a side wall, a top wall, a bottom wall and a cavity, said top wall having an opening into said cavity, said cavity designed to at least partially telescopically receive said lower portion of said implant, said cavity including a connection arrangement to secure said implant to said sleeve;
  c) forming an opening in said bone or cartilage of said spine;
  d) inserting said bottom wall and at least a portion of said side wall of said sleeve into said opening, said step of inserting said sleeve into said opening of said bone or cartilage includes a) placing said bottom wall of said sleeve at the top of said opening in said bone or cartilage, b) moving a medical instrument into contact with said top wall of said sleeve, c) rotating said sleeve by said medical instrument to cause said side wall of said sleeve to be at least partially inserted in said opening of said bone or cartilage, and d) removing a cap from said top wall of said sleeve after said side wall of said sleeve to be at least partially inserted in said opening of said bone or cartilage, said cap designed to cover said opening into said cavity while said sleeve is at least partially inserted in said opening of said bone or cartilage;

e) securing said sleeve to said bone and/or cartilage of said spine;
f) inserting at least a portion of said lower portion of said implant into said cavity of said sleeve and securing said implant to said sleeve; and,
g) pumping fluid from said implant into said cavity of said sleeve and then allowing said fluid to flow through a plurality of passageways in said sleeve so that said fluid contacts said bone or cartilage located about said sleeve, one or more of said passageways on said sleeve located in a region selected from the group consisting of said bottom wall and said side wall, said plurality of passageways fluidly connecting said cavity of said sleeve to an outer surface of said sleeve, said fluid formulated to facilitate in at least one function selected from the group consisting of healing said bone or cartilage about said sleeve and promoting growth of said bone or cartilage about said sleeve.

23. The method as defined in claim 22, wherein an outer surface of said outer wall of said sleeve includes a thread, said thread designed to facilitate in the connection between said sleeve and said bone or cartilage.

24. The method as defined in claim 23, wherein said side wall of said sleeve includes a side slot that extends at least partially along the longitudinal length of said side wall, said side slot designed to enable said sleeve to change a cross-sectional area of said sleeve as said sleeve is inserted into said opening of said bone or cartilage.

25. A method of connecting an implant to a bone or cartilage of a spine comprising:
    a) selecting an implant, said implant including a head and a lower portion connected to the head, said head including at least one arrangement selected from a group consisting of a) connector to connect to a support structure used for a spine, b) a current generating device that directs current from the implant to the bone or cartilage of the spine, and c) a pump device that directs fluid from the implant to the bone or cartilage of the spine;
    b) selecting a sleeve that includes a side wall, a top wall, a bottom wall and a cavity, said top wall having an opening into said cavity, said cavity designed to at least partially telescopically receive said lower portion of said implant, said cavity including a connection arrangement to secure said implant to said sleeve;
    c) forming an opening in said bone or cartilage of said spine;
    d) inserting said bottom wall and at least a portion of said side wall of said sleeve into said opening, said step of inserting said sleeve into said opening of said bone or cartilage includes a) placing said bottom wall of said sleeve at the top of said opening in said bone or cartilage, b) moving a medical instrument into contact with said top wall of said sleeve, c) rotating said sleeve by said medical instrument to cause said side wall of said sleeve to be at least partially inserted in said opening of said bone or cartilage, and d) removing a cap from said top wall of said sleeve after said side wall of said sleeve to be at least partially inserted in said opening of said bone or cartilage, said cap designed to cover said opening into said cavity while said sleeve is at least partially inserted in said opening of said bone or cartilage;
    e) securing said sleeve to said bone and/or cartilage of said spine;
    f) inserting at least a portion of said lower portion of said implant into said cavity of said sleeve and securing said implant to said sleeve; and,
    g) transferring current from said implant to said sleeve, said sleeve including an electrically conducting material that enables current to flow from said implant to said sleeve and then to said bone or cartilage located about said sleeve, said current designed to facilitate in at least one function selected from the group consisting of healing said bone or cartilage about said sleeve and promoting growth of said bone or cartilage about said sleeve.

26. The method as defined in claim 25, wherein an outer surface of said outer wall of said sleeve includes a thread, said thread designed to facilitate in the connection between said sleeve and said bone or cartilage.

27. The method as defined in claim 26, wherein said side wall of said sleeve includes a side slot that extends at least partially along the longitudinal length of said side wall, said side slot designed to enable said sleeve to change a cross-sectional area of said sleeve as said sleeve is inserted into said opening of said bone or cartilage.

28. A method of connecting an implant to a bone or cartilage of a spine comprising:
    a) selecting an implant, said implant including a head and a lower portion connected to the head, said head including at least one arrangement selected from a group consisting of a) connector to connect to a support structure used for a spine, b) a current generating device that directs current from the implant to the bone or cartilage of the spine, and c) a pump device that directs fluid from the implant to the bone or cartilage of the spine;
    b) selecting a sleeve that includes a side wall, a top wall, a bottom wall and a cavity, said top wall having an opening into said cavity, said cavity designed to at least partially telescopically receive said lower portion of said implant, said cavity including a connection arrangement to secure said implant to said sleeve;
    c) forming an opening in said bone or cartilage of said spine;
    d) inserting said bottom wall and at least a portion of said side wall of said sleeve into said opening, said step of inserting said sleeve into said opening of said bone or cartilage includes a) placing said bottom wall of said sleeve at the top of said opening in said bone or cartilage, b) moving a medical instrument into contact with said top wall of said sleeve, c) rotating said sleeve by said medical instrument to cause said side wall of said sleeve to be at least partially inserted in said opening of said bone or cartilage, and d) removing a cap from said top wall of said sleeve after said side wall of said sleeve to be at least partially inserted in said opening of said bone or cartilage, said cap designed to cover said opening into said cavity while said sleeve is at least partially inserted in said opening of said bone or cartilage;
    e) securing said sleeve to said bone and/or cartilage of said spine; and,
    f) inserting at least a portion of said lower portion of said implant into said cavity of said sleeve and securing said implant to said sleeve;
    g) pumping fluid from said implant into said cavity of said sleeve and then allowing said fluid to flow through a plurality of passageways in said sleeve so that said fluid contacts said bone or cartilage located about said sleeve, one or more of said passageways on said sleeve located in a region selected from the group consisting of said bottom wall and said side wall, said plurality of passageways fluidly connecting said cavity of said sleeve to an outer surface of said sleeve, said fluid formulated to facilitate in at least one function selected from the group consisting of healing said bone or cartilage about said sleeve and promoting growth of said bone or cartilage about said sleeve; and, h) transferring current from said implant to said sleeve, said sleeve including an electrically conducting material that enables current to flow from said implant to said sleeve and then to said bone or cartilage located about said sleeve, said current designed to facilitate in at least one function selected from the group consisting of healing said bone or cartilage about said sleeve and promoting growth of said bone or cartilage about said sleeve.

29. The method as defined in claim 28, wherein an outer surface of said outer wall of said sleeve includes a thread, said thread designed to facilitate in the connection between said sleeve and said bone or cartilage.

30. The method as defined in claim 29, wherein said side wall of said sleeve includes a side slot that extends at least partially along the longitudinal length of said side wall, said side slot designed to enable said sleeve to change a cross-sectional area of said sleeve as said sleeve is inserted into said opening of said bone or cartilage.

* * * * *